(12) United States Patent
Chen et al.

(10) Patent No.: US 7,468,386 B2
(45) Date of Patent: *Dec. 23, 2008

(54) PYRAZOLE-AMINE COMPOUNDS FOR THE TREATMENT OF NEURODEGENERATIVE DISORDERS

(75) Inventors: Yuhpyng L. Chen, Waterford, CT (US); Lei Zhang, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/773,831

(22) Filed: Jul. 5, 2007

(65) Prior Publication Data
US 2007/0265327 A1    Nov. 15, 2007

Related U.S. Application Data

(63) Continuation of application No. 11/078,861, filed on Mar. 11, 2005, now Pat. No. 7,244,757.

(60) Provisional application No. 60/558,904, filed on Apr. 1, 2004.

(51) Int. Cl.
A61K 31/415    (2006.01)
A61K 31/4155    (2006.01)
C07D 231/40    (2006.01)

(52) U.S. Cl. .................. 514/407; 548/371.7; 548/365.7; 548/364.4

(58) Field of Classification Search ................ 514/407; 548/371.7, 365.7, 364.4
See application file for complete search history.

(56) References Cited

U.S. PATENT DOCUMENTS 7,244,757 B2    7/2007    Chen et al.

FOREIGN PATENT DOCUMENTS

| JP | 43006621 | 3/1968 |
|---|---|---|
| JP | 48010069 | 2/1973 |
| WO | WO01/12188 | 2/2001 |
| WO | WO02/18346 | 3/2002 |
| WO | WO02/48114 | 6/2002 |
| WO | WO03/064396 | 8/2003 |
| WO | WO03/094854 | 11/2003 |
| WO | WO2004/033434 | 4/2004 |
| WO | WO2004/099200 | 11/2004 |
| WO | WO2005/009344 | 2/2005 |

OTHER PUBLICATIONS

Citron, M., "Strategies For Disease Modification in Alzheimer's Disease," *Nature Revues Neuroscience*, 2004, 677-685.
Masters, C., et al., "Amyloid Plaque Core Protein In Alzheimer Disease And Down Syndrome" *Proc. Natl. Acad. Sci. USA*, 1985, 4245-4249, vol. 82.
Tanzi, R., "Neuropathology In The Down's Syndrome Brain," *Nature Medicine*, 1996, 31-32, vol. 2 No. 1. 1996, 677-685, vol. 5.
Wise, L., et al., "(5-Amino-1,3_Dimethyl-1H-Pyrazol-4-)(2-Fluorophenyl) Methanones. A Series Of Novel Potential Antipsychotic Agents," *Journal Of Medicinal Chemistry*, 1986, 1628-1637, vol. 29.
XP-002346273, File Caplus, Stn CA Caesar Accession No. 1145, 1968:506704, p. 1-2, Pyrazole Derivatives, Kameyama, Tsutomu, et al., Takeda Chemical Industries, Ltd., JPN. Tokyo, Koho, 9 pp. 1968.

*Primary Examiner*—Kamal A Saeed
*Assistant Examiner*—Jason Nolan
(74) *Attorney, Agent, or Firm*—Bryan C. Zielinski; Jeffrey H. Tidwell

(57) ABSTRACT

The present invention relates to compounds of the Formula

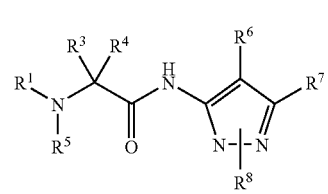

I wherein $R^1$, $R^3$, $R^4$, $R^5$, $R^6$, $R^7$ and $R^8$ are as defined. Compounds of the Formula I have activity inhibiting production of Aβ-peptide. The invention also relates to pharmaceutical compositions and methods of treating disorders and diseases, for example, neurodegenerative and/or neurological disorders, e.g., Alzheimer's disease, in a mammal comprising compounds of the Formula I.

11 Claims, No Drawings

PYRAZOLE-AMINE COMPOUNDS FOR THE TREATMENT OF NEURODEGENERATIVE DISORDERS

CROSS REFERENCE TO RELATED APPLICATION

This application is a continuation of U.S. patent application Ser. No. 11/078,861, filed Mar. 11, 2005, now U.S. Pat. No. 7,244,757, which claims the benefit of U.S. Provisional Patent Application No. 60/558,904, filed Apr. 1, 2004, all of which are herein incorporated by reference in their entirety.

FIELD OF THE INVENTION

The present invention relates to the treatment of neurodegenerative and/or neurological disorders, such as Alzheimer's disease, in mammals, including humans. This invention also relates to inhibiting, in mammals, including humans, the production of Aβ-peptides that can contribute to the formation of neurological deposits of amyloid protein. More particularly, this invention relates to pyrazole-amine compounds, pharmaceutical compositions comprising such compounds and methods of using such compounds, i.e., for the treatment of neurodegenerative and/or neurological disorders, such as Alzheimer's disease, related to Aβ-peptide production.

BACKGROUND OF THE INVENTION

Dementia results from a wide variety of distinctive pathological processes. The most common pathological processes causing dementia are Alzheimer's disease (AD), cerebral amyloid angiopathy (CAA) and prion-mediated diseases. AD affects nearly half of all people past the age of 85, the most rapidly growing portion of the United States population. As such, the number of AD patients in the United States is expected to increase from about 4 million to about 14 million by the middle of the next century.

Treatment of AD typically is the support provided by a family member in attendance. Stimulated memory exercises on a regular basis have been shown to slow, but not stop, memory loss. A few drugs, for example Aricept™, provide treatment of AD.

A hallmark of AD is the accumulation in the brain of extracellular insoluble deposits called amyloid plaques and abnormal lesions within neuronal cells called neurofibrillary tangles. Increased plaque formation is associated with an increased risk of AD. Indeed, the presence of amyloid plaques, together with neurofibrillary tangles, is the basis for definitive pathological diagnosis of AD.

The major components of amyloid plaques are the amyloid Aβ-peptides, also called Aβ-peptides, that consist of several proteins including 38, 40, 42 or 43 amino acids, designated as the $A\beta_{1-38}$, $A\beta_{1-40}$, $A\beta_{1-42}$ and $A\beta_{1-43}$ peptides, respectively. The Aβ-peptides are thought to cause nerve cell destruction, in part, because they are toxic to neurons in vitro and in vivo.

The Aβ peptides are derived from larger amyloid precursor proteins (APP proteins), that consist of four proteins containing 695, 714, 751 or 771 amino acids, designated as the $APP_{695}$, $APP_{714}$, $APP_{751}$ and $APP_{771}$, respectively. Proteases are believed to produce the Aβ peptides by cleaving specific amino acid sequences within the various APP proteins. The proteases are named "secretases" because the Aβ-peptides they produce are secreted by cells into the extracellular environment. These secretases are each named according to the cleavage(s) they make to produce the Aβ-peptides. The secretase that forms the amino terminal end of the Aβ-peptides is called the beta-secretase. The secretase that forms the carboxyl terminal end of the Aβ-peptides is called the gamma-secretase.

This invention relates to novel compounds that inhibit Aβ-peptide production, to pharmaceutical compositions comprising such compounds, and to methods of using such compounds to treat neurodegenerative and/or neurological disorders.

SUMMARY OF THE INVENTION

The present invention relates to compounds of the Formula I

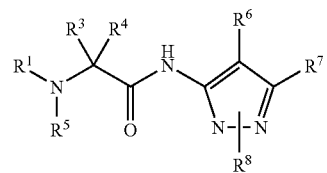

I wherein $R^1$ is selected from —$C_1$-$C_{20}$ alkyl, —$C_2$-$C_{20}$ alkenyl, —$C_2$-$C_{20}$ alkynyl, —$C_3$-$C_8$ cycloalkyl, —$C_4$-$C_8$ cycloalkenyl, —($C_5$-$C_{11}$)bi- or tricycloalkyl, —($C_7$-$C_{11}$)bi- or tricycloalkenyl, -(3-8 membered) heterocycloalkyl, -(5-11 membered) heterobicycloalkyl, —$C_6$-$C_{14}$ aryl and -(5-14 membered) heteroaryl, wherein each hydrogen atom of said alkyl, alkenyl and alkynl of $R^1$ is optionally independently replaced with a —F;

and wherein when $R^1$ is alkyl, alkenyl or alkynyl, $R^1$ is optionally independently substituted with from one to three substituents $R^{1a}$, and wherein when $R^1$ is cycloalkyl, cycloalkenyl, bi- or tricycloalkyl, bi- or tricycloalkenyl, heterocycloalkyl, aryl or heteroaryl, $R^1$ is optionally independently substituted with from one to three substituents $R^{1b}$;

$R^{1a}$ is in each instance independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_8$ alkenoxy, —$C_2$-$C_6$ alkynoxy, —Cl, —Br, —I, —OH, —CN, —$NO_2$, —$NR^9R^{10}$, —C(=O)$NR^9R^{10}$, —S(O)$_2NR^9R^{10}$, —C(=O)$R^{11}$, —S(O)$_nR^{11}$, —C(=O)$OR^{12}$, —$C_3$-$C_8$ cycloalkyl, —$C_4$-$C_8$ cycloalkenyl, —($C_5$-$C_{11}$)bi- or tricycloalkyl, —($C_7C_{11}$)bi- or tricycloalkenyl, -(3-8 membered) heterocycloalkyl, —C6-C14 aryl, -(5-14 membered) heteroaryl, —C6-C14 aryloxy and -(5-14 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of R1a are each optionally independently substituted with from one to three substituents R1b;

$R^{1b}$ is in each instance independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —F, —Cl, —Br, —I, —CN, —$NO_2$, —($C_{zero}$-$C_4$ alkylene)-$NR^9R^{10}$, —($C_{zero}$-$C_4$ alkylene)-C(=O)$NR^9R^{10}$, —($C_{zero}$-$C_4$ alkylene)-C(=O)$R^{11}$, —($C_{zero}$-$C_4$ alkylene)-C(=O)$OR^{12}$, —($C_{zero}$-$C_4$ alkylene)-S(O)$_nR^{11}$, —($C_{zero}$-$C_4$ alkylene)-S(O)$_2NR^9R^{10}$, —($C_{zero}$-$C_4$ alkylene)-OH, —$C_1$-$C_6$ hydroxyalkyl, —$C_6$-$C_{14}$ aryl, -(5-15 membered) heteroaryl, —$C_6$-$C_{14}$ aryloxy and -(5-14 membered) heteroaryloxy, wherein said alkyl, alkenyl and alkynyl of $R^{1b}$ are each optionally independently substituted with from one to six substituents independently selected from —F, —Cl, —Br and —I;

$R^3$ is selected from $C_1$-$C_6$ alkyl, —$C_2$-$C_6$ alkenyl, —$C_2C_6$ alkynyl, —($C_{zero}$-$C_4$ alkylene)-($C_3$-$C_6$ cycloalkyl) and —($C_{zero}$-$C_4$ alkylene)-($C_3$-$C_6$ cycloalkenyl), wherein said alkyl, alkenyl and alkynyl of $R^3$ are each optionally independently substituted with a substituent selected from —OH, —$C_1$-$C_4$ alkoxy and —S—($C_1$-$C_4$ alkyl);

$R^4$ is —H, —F or —$C_1$-$C_4$ alkyl;

or $R^3$ and $R^4$ together with the carbon atom to which they are both attached may optionally form a cyclopropyl, cyclobutyl, cyclopentyl, cyclohexyl, morpholino, piperidino or perhydro-2H-pyran moiety, wherein said moiety formed by $R^3$ and $R^4$ is optionally independently substituted with from one to three substituents independently selected from methyl, ethyl, allyl, methoxy, ethoxy, —F, —Cl, —OH, —CN, —$CF_3$ and —$OCF_3$;

$R^5$ is selected from —H, —$C_1$-$C_6$ alkyl and —$C_6$-$C_{10}$ aryl, wherein said alkyl and aryl of $R^5$ are each optionally independently substituted with from one to three substituents $R^{1a}$;

or $R^5$ and $R^1$ together with the nitrogen atom to which they are both attached may optionally form a -(5-8 membered) heterocycloalkyl, -(5-8 membered) heterocycloalkenyl or (5-14 membered) heteroaryl, wherein said heterocycloalkyl, heterocycloalkenyl and heteroaryl optionally contains one or two further heteroatoms selected from N, O, and S, and wherein said heterocycloalkyl, heterocycloalkenyl and heteroaryl is optionally independently substituted with from one to three substituents $R^{1b}$;

$R^6$ is selected from —H, —$C_1$-$C_{20}$ alkyl, —Cl, —F, —Br, —I, —CN, —$CF_3$, —C(=O)$R^{11}$, —C(=O)$OR^{12}$, —$S(O)_2$$NR^9R^{10}$, —$S(O)_nR^{11}$, —C(=$NR^9$)$R^{15}$, —$C_3$-$C_{12}$ cycloalkyl, —$C_4$-$C_{12}$ cycloalkenyl, and —$C_6$-$C_{10}$ aryl, wherein said alkyl, cycloalkyl, cycloalkenyl and aryl of $R^6$ are each optionally independently substituted with from one to three substituents $R^{1b}$;

$R^7$ is selected from H, —$C_1$-$C_{20}$ alkyl, —$C_2$-$C_{20}$ alkenyl, —$C_2$-$C_{20}$ alkynyl, —$C_1$-$C_{20}$ alkoxy, —$C_2$-$C_{20}$ alkenoxy, —$C_2$-$C_{20}$ alkynoxy, —F, —Cl, —Br, —I, —CN, —$NO_2$, —$CF_3$, —$NR^{14}R^{15}$, —C(=O)$NR^{14}R^{15}$, —C(=O)$R^{13}$, —$S(O)_nR^{13}$, —C(=O)$OR^{13}$, —C(=$NR^9$)$R^{15}$, —$S(O)_2$$NR^{14}R^{15}$, —($C_{zero}$-$C_4$ alkylene)-($C_3$-$C_{12}$ cycloalkyl), —($C_{zero}$-$C_4$ alkylene)-(($C_4$-$C_{12}$)cycloalkenyl), —($C_{zero}$-$C_4$ alkylene)-(($C_5$-$C_{20}$)bi- or tricycloalkyl), —($C_{zero}$-$C_4$ alkylene)-($C_7$-$C_{20}$ bi- or tricycloalkenyl), —($C_{zero}$-$C_4$ alkylene)-((3-12 membered) heterocycloalkyl), —($C_{zero}$-$C_4$ alkylene)-((7-20 membered) heterobi- or heterotricycloalkyl), —($C_{zero}$-$C_4$ alkylene)-($C_6$-$C_{14}$ aryl) and —($C_{zero}$-$C_4$ alkylene)-((5-15 membered) heteroaryl), wherein each hydrogen atom of said alkyl, alkenyl, alkynyl, alkoxy, alkenoxy and alkynoxy of $R^7$ is optionally independently replaced with a —F, and wherein said cycloalkyl, cycloalkenyl, bi- or tricycloalkyl, bi- or tricycloalkenyl, heterocycloalkyl, aryl and heteroaryl of $R^7$ are each optionally independently substituted with from one to six —F, and wherein $R^7$ is optionally independently substituted with from one to three substituents independently selected from $R^{1a}$, —$(CH_2)_{1-10}NR^9R^{10}$, —$C_3$-$C_{12}$ cycloalkyl, -(4-12 membered) heterocycloalkyl, —$C_6$-$C_{14}$ aryl, -(5-15 membered) heteroaryl, -(4-12 membered) heterocycloalkoxy, —$C_6$-$C_{12}$ aryloxy and -(5-12 membered) heteroaryloxy;

or $R^6$ and $R^7$ together with the carbon atoms to which they are respectively attached may optionally form a —$C_6$-$C_{10}$ aryl, —$C_6$-$C_8$ cycloalkyl, —$C_6$-$C_8$ cycloalkenyl, -(5-8 membered) heterocycloalkyl, -(5-8 membered) heterocycloalkenyl, —$C_{10}$-$C_{14}$ bicycloalkyl, —$C_{10}$-$C_{14}$ bicycloalkenyl, -(10-14 membered) bicycloheteroalkyl or -(10-14 membered) bicycloheteroalkenyl fused to the pyrazole ring of Formula I, wherein said heterocycloalkyl and heterocycloalkenyl each independently contain from one to three heteroatoms independently selected from N, O and S, and wherein said bicycloheteroalkyl and bicycloheteroalkenyl each independently contain from one to five heteroatoms selected independently from N, O and S, and wherein said cycloalkyl, cycloalkenyl, heterocycloalkyl, heterocycloalkenyl, bicycloalkyl, bicycloalkenyl, bicycloheteroalkyl, bicycloheteroalkenyl and aryl are each optionally independently substituted with from one to three substituents $R^{1b}$;

or $R^7$ together with the carbon atom to which it is attached and together with the nitrogen atom of the pyrazole ring of Formula I adjacent to said carbon atom to which $R^7$ is attached may optionally form a -(5-8 membered) heterocycloalkyl, -(5-8 membered) heterocycloalkenyl, -(10-14 membered) bicycloheteroalkyl or -(10-14 membered) bicycloheteroalkenyl fused to the pyrazole ring of Formula I, wherein said heterocycloalkyl and heterocycloalkenyl each independently contain from one to three heteroatoms independently selected from N, O and S, and wherein said bicycloheteroalkyl and bicycloheteroalkenyl each independently contain from one to five heteroatoms independently selected from N, O and S, and wherein said heterocycloalkyl, heterocycloalkenyl, bicycloheteroalkyl and bicycloheteroalkenyl are each optionally independently substituted with from one to three substituents $R^{1b}$;

$R^8$ is selected from —H, —$C_1$-$C_4$ alkyl, —$CF_3$, —C(=O)$R^{11}$, —C(=O)$OR^{12}$ and —$C_6$-$C_{10}$ aryl, with the proviso that the pyrazole ring of Formula I is always aromatic and that $R^8$ is attached to either nitrogen in the pyrazole ring of Formula I;

$R^9$ and $R^{10}$ are each independently selected from —H, —$C_1$-$C_8$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —OH, —C(=O)$R^{11}$, —$S(O)_nR^{11}$, —C(=O)$OR^{12}$, —$S(O)_2$$NR^{11}R^{12}$, —($C_{zero}$-$C_4$ alkylene)-($C_3$-$C_8$ cycloalkyl), —($C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), —($C_{zero}$-$C_4$ alkylene)-(($C_7$-$C_{11}$)bi- or tricycloalkenyl), —($C_{zero}$-$C_4$ alkylene)-((3-8 membered) heterocycloalkyl), —($C_{zero}$-$C_4$ alkylene)-($C_6$-$C_{14}$ aryl) and —($C_{zero}$-$C_4$ alkylene)-((5-14 membered) heteroaryl), wherein each hydrogen atom of said alkyl, alkenyl, alkynyl, alkoxy, alkenoxy and alkynoxy of $R^9$ and $R^{10}$ is optionally independently replaced with a —F, and wherein said cycloalkyl, cycloalkenyl, bi- or tricycloalkyl, bi- or tricycloalkenyl, heterocycloalkyl, aryl and heteroaryl of $R^9$ and $R^{10}$ are each optionally independently substituted with from one to three substituents independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —F, —Cl, —Br, —I, —OH, —CN, —$NO_2$, —$NR^{14}R^{15}$, —C(=O)$NR^{14}R^{15}$, —C(=O)$R^{11}$, —C(=O)$OR^{12}$, —$S(O)_nR^{11}$, —$S(O)_2$$NR^{14}R^{15}$, —$C_1$-$C_6$ hydroxyalkyl, —($C_6$-$C_{14}$) aryloxy, -(5-14 membered) heteroaryloxy, —($C_{zero}$-$C_4$)—(($C_6$-$C_{14}$) aryl), —($C_{zero}$-$C_4$)-(5-14 membered heteroaryl), and wherein said alkyl, alkenyl and alkynl substituents of $R^9$ and $R^{10}$ are each optionally independently further substituted with from one to six atoms independently selected from —F, —Cl, —Br and —I;

or $NR^9R^{10}$ may optionally form a -(4-7 membered) heterocycloalkyl or -(4-7 membered) heterocycloalkenyl, wherein said heterocycloalkyl and heterocycloalkenyl each optionally independently contain one or two further heteroatoms independently selected from N, O, and S, and wherein said heterocycloalkyl and heterocycloalkenyl are each optionally independently substituted with from one to three substituents independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-

$C_6$ alkynoxy, —$C_1$-$C_6$ hydroxyalkyl, —$C_2$-$C_6$ hydroxyalkenyl, —$C_2$-$C_6$ hydroxyalkynyl, —F, —Cl, —Br, —I, —OH, —CN, —NO$_2$, —NR$^{14}$R$^{15}$, —C(=O)NR$^{14}$R$^{15}$, —C(=O)R$^{11}$, —C(=O)OR$^{12}$, —S(O)$_n$R$^{11}$, —S(O)$_2$NR$^{14}$R$^{15}$, —($C_{zero}$-$C_4$)—($C_6$-$C_{14}$ aryl), —($C_{zero}$-$C_4$)-((5-14 membered) heteroaryl), —$C_6$-$C_{14}$ aryloxy and -(5-14 membered) heteroaryloxy, and wherein said —$C_1$-$C_6$ alkyl, —$C_2$-$C_6$ alkenyl and —$C_2$-$C_6$ alkynyl substituents of NR$^9$R$^{10}$ are each optionally independently further substituted with from one to six atoms independently selected from —F, —Cl, —Br and —I;

R$^{11}$ and R$^{12}$ are each independently selected from H, —$C_1$-$C_6$ alkyl, —($C_{zero}$-$C_4$ alkylene)-($C_3$-$C_8$ cycloalkyl), —($C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), and —($C_{zero}$-$C_4$ alkylene)-(($C_7$-$C_{11}$)bi- or tricycloalkenyl), —($C_{zero}$-$C_4$ alkylene)-((3-8 membered) heterocycloalkyl), —($C_{zero}$-$C_4$ alkylene)-($C_6$-$C_{10}$ aryl) and —($C_{zero}$-$C_4$ alkylene)-((5-14 membered) heteroaryl), wherein R$^{11}$ and R$^{12}$ are each optionally independently substituted with from one to three substituents independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —NO$_2$, —CF$_3$, —NR$^{14}$R$^{15}$, —C(=O)NR$^{14}$R$^{15}$, —SO$_2$NR$^{14}$R$^{15}$, —C(=O)H, —C(=O)OH and —C(=O)O($C_1$-$C_6$ alkyl), and wherein said alkyl, alkenyl and alkynyl substituents of R$^{11}$ and R$^{12}$ are each optionally independently further substituted with from one to six —F, or with from one to two substituents independently selected from —$C_1$-$C_4$ alkoxy, or with an —OH;

R$^{13}$ is selected from —H, —$C_1$-$C_6$ alkyl, —$C_2$-$C_6$ alkenyl, and —$C_2$-$C_6$ alkynyl, —($C_{zero}$-$C_4$ alkylene)-($C_3$-$C_{12}$ cycloalkyl), —($C_{zero}$-$C_4$ alkylene)-($C_4$-$C_{12}$ cycloalkenyl), —($C_{zero}$-$C_4$ alkylene)-(($C_5$-$C_{20}$)bi- or tricycloalkyl), —($C_{zero}$-$C_4$ alkylene)-(($C_7$-$C_{20}$)bi- or tricycloalkenyl), —($C_{zero}$-$C_4$ alkylene)-((3-12 membered) heterocycloalkyl), —($C_{zero}$-$C_4$ alkylene)-((7-20 membered) heterobi- or heterotricycloalkyl), —($C_{zero}$-$C_4$ alkylene)-($C_6$-$C_{14}$ aryl) and —($C_{zero}$-$C_4$ alkylene)-((5-14 membered) heteroaryl), wherein each hydrogen atom of said alkyl alkenyl and alkynyl of R$^1$ is optionally independently replaced with a —F, and wherein R$^{13}$ is optionally independently substituted with from one to three substituents independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —NO$_2$, —CF$_3$, —NR$^{14}$R$^{15}$, —C(=O)N NR$^{14}$R$^{15}$, —SO$_2$NR$^{14}$R$^{15}$, —C(=O)H, —C(=O)OH and —C(=O)O($C_1$-$C_6$ alkyl), wherein said alkyl, alkenyl and alkynyl substituents of R$^{13}$ are each optionally independently further substituted with from one to six —F, or with from one to two substituents independently selected from —$C_1$-$C_4$ alkoxy, or with an —OH;

R$^{14}$ and R$^{15}$ are each independently selected from —H, —$C_1$-$C_{20}$ alkyl, -$C_2$-$C_{20}$ alkenyl, —$C_2$-$C_{20}$ alkynyl, —C(=O)R$^{11}$, —S(O)$_n$R$^{11}$, —C(=O)OR$^{12}$, —S(O)$_2$NR$^{11}$R$^{12}$, —($C_{zero}$-$C_4$ alkylene)-($C_3$-$C_{12}$ cycloalkyl), —($C_{zero}$-$C_4$ alkylene)-($C_4$-$C_{12}$ cycloalkenyl), —($C_{zero}$-$C_4$ alkylene)-(($C_5$-$C_{20}$)bi- or tricycloalkyl), —($C_{zero}$-$C_4$ alkylene)-(($C_7$-$C_{20}$)bi- or tricycloalkenyl), —($C_{zero}$-$C_4$ alkylene)-((3-8 membered) heterocycloalkyl), —($C_{zero}$-$C_4$ alkylene)-($C_6$-$C_{14}$ aryl) and —($C_{zero}$-$C_4$ alkylene)-((5-14 membered) heteroaryl), wherein each hydrogen atom of said alkyl, alkenyl and alkynyl of R$^{14}$ and R$^{15}$ is optionally independently replaced with a —F, and wherein said cycloalkyl, cycloalkenyl, bi- or tricycloalkyl, bi- or tricycloalkenyl, heterocycloalkyl, aryl and heteroaryl of R$^{14}$ and R$^{15}$ are each optionally independently substituted with from one to three substituents independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkynyl, —F, —Cl, —Br, —I, —OH, —CN, —NO$_2$, —NH$_2$, —C(=O)H, —S(O)$_n$H, —C(=O)OH, —C(=O)NH$_2$, —S(O)$_2$NH$_2$, —($C_{zero}$-$C_4$ alkylene)-($C_6$-$C_{14}$ aryl), —($C_{zero}$-$C_4$ alkylene)-((5-14 membered) heteroaryl), —$C_6$-$C_{14}$ aryloxy and -(5-14 membered) heteroaryloxy, wherein each hydrogen atom of said alkyl, alkenyl, alkynl, alkoxy, alkenoxy, alkynoxy, hydroxyalkyl, hydroxyalkenyl and hydroxyalkynyl substituent of R$^{14}$ and R$^{15}$ is optionally independently replaced with a —F, and wherein said alkyl, alkenyl and alkynyl substituents of R$^{14}$ and R$^{15}$ are each optionally independently further substituted with from one to six atoms independently selected from —Cl, —Br and —I;

or NR$^{14}$R$^{15}$ may optionally independently form a (4-7 membered) heterocycloalkyl or (4-7 membered) heterocycloalkenyl, wherein said heterocycloalkyl and heterocycloalkenyl optionally independently contains from one to two further heteroatoms independently selected from N, O, and S, and wherein said heterocycloalkyl and heterocycloalkenyl is optionally independently substituted with one to three substituents independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkynyl, —F, —Cl, —Br, —I, —OH, —CN, —NO$_2$, —NH$_2$, —C(=O)H, —S(O)$_n$H, —C(=O)OH, —C(=O)NH$_2$, —S(O)$_2$NH$_2$, —($C_{zero}$-$C_4$ alkylene)($C_6$-$C_{14}$ aryl), —($C_{zero}$-$C_4$ alkylene)-((5-14 membered) heteroaryl), —$C_6$-$C_{14}$ aryloxy and -(5-14 membered) heteroaryloxy, and wherein each hydrogen atom of said alkyl, alkenyl, alkynyl, alkoxy, alkenoxy, alkynoxy, hydroxyalkyl, hydroxyalkenyl and hydroxyalkynyl substituent of NR$^{14}$R$^{15}$ is optionally independently replaced with a —F, and wherein said alkyl, alkenyl and alkynyl substituents of NR$^{14}$R$^{15}$ are each optionally independently further substituted with from one to six substituents independently selected from —Cl, —Br, and —I; and n is in each instance an integer independently selected from zero, 1, 2 and 3;

or the pharmaceutically acceptable salts of such compounds.

Compounds of the Formula I may have optical centers and therefore may occur in different enantiomeric and diastereomeric configurations. The present invention includes all enantiomers, diastereomers, and other stereoisomers of such compounds of the Formula I, as well as racemic compounds and racemic mixtures and other mixtures of stereoisomers thereof.

Pharmaceutically acceptable salts of the compounds of Formula I include the acid addition and base salts thereof.

Suitable acid addition salts are formed from acids which form non-toxic salts. Examples include, but are not limited to, the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandelates mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, salicylate, saccharate, stearate, succinate, sulfonate, stannate, tartrate, tosylate, trifluoroacetate and xinofoate salts.

Suitable base salts are formed from bases which form non-toxic salts. Examples include, but are not limited to, the aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)_3$) polar head group. For more information, see Crystals and the Polarizing Microscope by N. H. Hartshorne and A. Stuart, $4^{th}$ Edition (Edward Arnold, 1970).

Hereinafter all references to compounds of Formula I include references to salts, solvates, multi-component complexes and liquid crystals thereof and to solvates, multi-component complexes and liquid crystals of salts thereof.

The compounds of the invention include compounds of Formula I as hereinbefore defined, including all polymorphs and crystal habits thereof, prodrugs and isomers thereof (including optical, geometric and tautomeric isomers) as hereinafter defined and isotopically-labeled compounds of Formula I.

Unless otherwise indicated, as used herein, the terms "halogen" and "halo" include F, Cl, Br, and I.

Unless otherwise indicated, as used herein, the term "alkyl" includes saturated monovalent hydrocarbon radicals having straight or branched moieties. Examples of alkyl groups include, but are not limited to, methyl, ethyl, n-propyl, isopropyl, cyclopropylmethylene (—$CH_2$-cyclopropyl) and t-butyl.

Unless otherwise indicated, as used herein, the term "alkenyl" includes alkyl moieties having at least one carbon-carbon double bond wherein alkyl is as defined above. Examples of alkenyl include, but are not limited to, ethenyl and propenyl.

Unless otherwise indicated, as used herein, the term "alkynyl" includes alkyl moieties having at least one carbon-carbon triple bond wherein alkyl is as defined above. Examples of alkynyl groups include, but are not limited to, ethynyl and 2-propynyl.

Unless otherwise indicated, as used herein, the term "alkoxy", means "alkyl-O-", wherein "alkyl" is as defined above. Examples of "alkoxy" groups include, but are not limited to, methoxy, ethoxy, propoxy, butoxy, pentoxy and allyloxy.

Unless otherwise indicated, as used herein, the term "alkenoxy", means "alkenyl-O-", wherein "alkenyl" is as defined above.

Unless otherwise indicated, as used herein, the term "alkynoxy", means "alkynyl-O-", wherein "alkynyl" is as defined above.

Unless otherwise indicated, as used herein, the term "cycloalkyl" includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" and "tricycloalkyl" groups include non-aromatic saturated cyclic alkyl moieties consisting of two or three rings respectively, wherein said rings share at least one carbon atom. "Bicycloalkyl" and "tricycloalkyl" groups also include cyclic moieties consisting of two or three rings respectively, wherein one ring is aryl or heteroaryl and wherein said rings share two carbon atoms. For purposes of the present invention, and unless otherwise indicated, bicycloalkyl groups include spiro groups and fused ring groups. Examples of bicycloalkyl groups include, but are not limited to, bicyclo-[3.1.0]-hexyl, bicyclo-2.2.1]-hept-1-yl, norbornyl, spiro[4.5]decyl, spiro[4.4]nonyl, spiro[4.3]octyl, spiro[4.2]heptyl, indan, teralene (1,2,3,4-tetrahydronaphlene) and 6,7,8,9-tetrahydro-5H-benzocycloheptene. An example of a tricycloalkyl group is adamantanyl. Other cycloalkyl, bicycloalkyl, and tricycloalkyl groups are known in the art, and such groups are encompassed by the definitions "cycloalkyl", "bicycloalkyl" and "tricycloalkyl" herein. "Cycloalkenyl", "bicycloalkenyl", and "tricycloalkenyl" refer to non-aromatic each cycloalkyl, bicycloalkyl, and tricycloalkyl moieties as defined above, except that they each include one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl, cyclobutenyl, and cyclohexenyl. A non-limiting example of a bicycloalkenyl group is norbornenyl. Cycloalkyl, cycloalkenyl, bicycloalkyl, and bicycloalkenyl groups also include groups that are substituted with one or more oxo moieties. Examples of such groups with oxo moieties are oxocyclopentyl, oxocyclobutyl, oxocyclopentenyl and norcamphoryl. Other cycloalkenyl, bicycloalkenyl, and tricycloalkenyl groups are known in the art, and such groups are included within the definitions "cycloalkenyl", "bicycloalkenyl" and "tricycloalkenyl" herein.

Unless otherwise indicated, as used herein, the term "aryl" includes an organic radical derived from an aromatic hydrocarbon by removal of one hydrogen, such as phenyl (Ph), naphthyl, indenyl, indanyl and fluorenyl. "Aryl" encompasses fused ring groups wherein at least one ring is aromatic.

Unless otherwise indicated, as used herein, the terms "heterocyclic" and "heterocycloalkyl" refer to non-aromatic cyclic groups containing one or more heteroatoms, preferably from one to four heteroatoms, each selected from O, S and N. "Heterobicycloalkyl" groups include non-aromatic two-ringed cyclic groups, wherein said rings share one or two atoms, and wherein at least one of the rings contains a heteroatom (O, S, or N). "Heterobicycloalkyl" groups also include two-ringed cyclic groups, wherein said one ring is aryl or heteroaryl ring and wherein said rings share one or two atoms, and wherein at least one of the rings contains a heteroatom (O, S, or N). Unless otherwise indicated, for purposes of the present invention, heterobicycloalkyl groups include spiro groups and fused ring groups. In one embodiment, each ring in the heterobicycloalkyl contains up to four heteroatoms (i.e. from zero to four heteroatoms, provided that at least one ring contains at least one heteroatom). The heterocyclic groups of this invention can also include ring systems substituted with one or more oxo moieties. Examples of non-aromatic heterocyclic groups are aziridinyl, azetidinyl, pyrrolidinyl, piperidinyl, azepinyl, piperazinyl, 1,2,3,6-tetrahydropyridinyt, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl, and 1,4-dioxaspiro[4.2]heptyl.

Unless otherwise indicated, as used herein, "heteroaryl" refers to aromatic groups containing one or more heteroatoms, preferably from one to four heteroatoms, selected from O, S and N. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroguinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, 1,2,4-trizainyl, 1,3,5-triazinyl, isoindolyl, 1-oxoisoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

Unless otherwise indicated, as used herein, the term "cycloalkoxy", means "cycloalkyl-O-", wherein "cycloalkyl" is as defined above.

Unless otherwise indicated, as used herein, the term "aryloxy", means "aryl-O-", wherein "aryl" is as defined above.

Unless otherwise indicated, as used herein, the term "heterocycloalkoxy", means "heterocycloalkyl-O-", wherein "heterocycloalkyl" is as defined above.

Unless otherwise indicated, as used herein, the term "heteroaryloxy", means "heteroaryl-O-", wherein "heteroaryl" is as defined above.

The foregoing groups, as derived from the compounds listed above, may be C-attached or N-attached where such is possible For instance, a group derived from pyrrole may be pyrrol-1-yl (N-attached) or pyrrol-3-yl (C-attached). The terms referring to the groups also encompass all possible tautomers.

In one aspect, the present invention relates to compounds of the Formula I, wherein $R^3$ is selected from methyl, ethyl, n-propyl, n-butyl, i-butyl, s-butyl, allyl and —$CH_2CH_2SCH_3$.

In another aspect, the present invention relates to compounds of the Formula I wherein $R^5$ is —H In another aspect, the present invention relates to compounds of the Formula I wherein $R^6$ is selected from —H, methyl, ethyl, —F, —Cl, —Br and —$CF_3$.

In another aspect, the present invention relates to compounds of the Formula I wherein $R^1$ is selected from —$C_2$-$C_{12}$ alkyl, —$C_3$-$C_8$ cycloalkyl, —$C_5$-$C_8$ cycloalkenyl, —($C_5$-$C_{11}$)bi- or tricycloalkyl, —($C_7$-$C_{11}$)bi- or tricycloalkenyl, (3-8 membered) heterocycloalkyl, (7-11 membered) heterobicycloalkyl, —$C_6$-$C_{10}$ aryl and -(5-10 membered) heteroaryl.

In another aspect, $R^1$ is $C_1$-$C_4$ alkyl substituted with $R^{1a}$, wherein $R^{1a}$ is selected from —($C_6$-$C_{10}$)aryl and -5-10 membered) heteroaryl.

In another aspect, $R^1$ is a straight-chain $C_2$-$C_{10}$ alkyl or branched $C_3$-$C_{10}$ alkyl.

In another aspect, $R^1$ is selected from —($C_7$-$C_{11}$)bi- or tricycloalkyl and (7-11 membered) heterobicycloalkyl.

In another aspect, $R^1$ is 1,2,3,4-tetrahydronaphthalenyl or indanyl, optionally substituted with 1 to 3 fluorine or chlorine atoms.

In another aspect, the present invention relates to compounds of the Formula I, wherein $R^7$ is selected from —H, —$C_1$-$C_{12}$ alkyl, —C2-$C_{12}$ alkenyl, —$C_1$-$C_{20}$ alkoxy, —C2-$C_{20}$ alkenoxy, —F, —Cl, —Br, —I, —CN, —$NO_2$, —$C_3$-$C_{12}$ cycloalkyl, -(3-12 membered) heterocycloalkyl, —$C_6$-$C_{14}$ aryl, -(5-15 membered) heteroaryl, —CHO, —C(=O)($C_1$-$C_{15}$ alkyl), —C(=O)((5-12 membered)heterocycloalkyl), —C(=O)($C_6$-$C_{14}$ aryl), —C(=O)((5-15 membered) heteroaryl), —C(=O)(C₅-C₁₂ cycloalkyl), —C(=O)O(C₁-C₈ alkyl), —C(=O)N(C₁-C₁₀ alkyl)(C₁-C₁₀ alkyl), —C(=O)N (C₁-C₁₀ alkyl)(C₆-C₁₀ aryl), —C(=O)NH(C₆-C₁₀ aryl), —C(=O)N(C₁-C₁₀ alkyl)((5-10 membered) heteroaryl), —C(=O)NH((5-10 membered) heteroaryl), —C(=O)N(C₁-C₁₀ alkyl)((5-10 membered) heterocycloalkyl), —C(=O) NH((5-10 membered) heterocycloalkyl), —C(=O)N(C₁-C₁₀ alkyl)(C₅-C₁₀ cycloalkyl), —C(=O)NH(C₅-C₁₀ cycloalkyl), —S(O)ₙ(C₁-C₁₅ alkyl), —S(O)ₙ(C₅-C₁₂ cycloalkyl), —S(O)ₙ (C₆-C₁₅ aryl) and —S(O)ₙ((5-10 membered) heteroaryl), wherein each hydrogen atom of said alkyl, alkenyl, alkoxy and alkenoxy of R⁷ is optionally independently replaced with a —F, and wherein said cycloalkyl and heterocycloalkyl of R⁷ are each optionally independently substituted with from one to six —F, and wherein said alkyl, alkenyl, cycloalkyl, heterocycloalkyl, aryl and heteroaryl of R⁷ are each optionally independently substituted with from one to three substituents independently selected from —C₁-C₆ alkoxy, —C₂-C₆ alkenoxy, —C2-C₆ alkynoxy, —F, —Cl, —Br, —I, —OH, —NR⁹R¹⁰, —(CH₂)₁₋₁₀NR⁹R¹⁰, —C(=O)R¹¹, —S(O)ₙR¹¹, —C(=O)OR¹¹, —C(=O) NR⁹R¹⁰, —S(O)₂NR⁹R¹⁰ —C₃-C₁₂ cycloalkyl, -(4-12 membered) heterocycloalkyl, -(4-12 membered) heterocycloalkoxy, —C₆-C₁₅ aryl, -(5-15 membered) heteroaryl, —C₆-C₁₂ aryloxy and -(6-12 membered) heteroaryloxy.

In another aspect, R⁷ is selected from —C₁-C₁₂ alkyl, —C2-C₁₂ alkenyl, —C₃-C₁₂ cycloalkyl and -(3-12 membered) heterocycloalkyl, wherein each hydrogen atom of said alkyl and alkenyl of R⁷ is optionally independently replaced with a —F, and wherein said cycloalkyl and heterocycloalkyl of R⁷ are each optionally substituted with from one to six —F, and wherein said alkyl, alkenyl, cycloalkyl and heterocycloalkyl of R⁷ are each optionally independently substituted with from one to three substituents independently selected from —OH, —C₁-C₆ alkoxy, —C2-C₆ alkenoxy, —C2-C₆ alkynoxy, —NR⁹R¹⁰, —(CH₂)₁₋₆NR⁹R¹⁰, —C(=O)R¹¹, —C(=O)OR¹¹, —C(=O)NR⁹R¹⁰, —S(O)₂NR⁹R¹⁰, -(4-12 membered) heterocycloalkoxy, —C₆-C₁₅ aryl, -(5-15 membered) heteroaryl, —C₆-C₁₂ aryloxy and -(6-12 membered) heteroaryloxy.

In another aspect, R⁷ is a —C₁-C₁₂ alkyl substituted with —NR⁹R¹⁰, morpholino, pyrrolidinyl or piperidinyl.

In another aspect, the compound of Formula I has the following stereoisomeric structure:

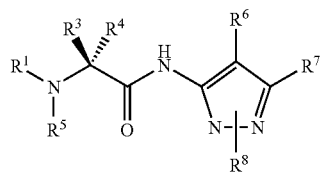

In another aspect, in the stereoisomeric compound above, R⁴ and R⁵ are hydrogen.

Specific embodiments of the present invention include the following compounds of Formula I, all pharmaceutically acceptable salts thereof, complexes thereof, and derivatives thereof that convert into a pharmaceutically active compound upon administration:

2-(S)-[2-(2,3-Difluoro-phenyl)-ethylamino]-pentanoic acid (5-phenyl-2H-pyrazol-3-yl)-amide;

2-(S)-Cyclohexylmethyl-amino)-pentanoic acid (5-phenyl-2H-pyrazol-3-yl)-amide;

2-(S)-Indan-2-ylamino)-pentanoic acid (5-phenyl-2H-pyrazol-3-yl)-amide;

2-(S)-1,2,3,4-Tetrahydro-naphthalen-2-ylamino)-pentanoic acid (5-phenyl-2H-pyrazol-3-yl)-amide;

2-(S)-2-Hydroxy-2-phenyl-ethylamino)-pentanoic acid (5phenyl-2H-pyrazol-3-yl)-amide;

2-(S)-2-Cyclohexyl-2-hydroxy-ethylamino)-pentanoic acid (5-phenyl-2H-pyrazol-3-yl)-amide;

2-(S)-Indan-1-ylamino)-pentanoic acid (5-phenyl-2H-pyrazol-3-yl)-amide;

2-(S)-5-Fluoro-indan-1-ylamino)-pentanoic acid (5-phenyl-2H-pyrazol-3-yl)-amide;

2-(S)-6-Bromo-1,2,3,4-tetrahydro-naphthalen-2-ylamino)pentanoic acid (5-phenyl-2H-pyrazol-3-yl)-amide;

2-(S)-3-Phenyl-indan-1-ylamino)-pentanoic acid (5-phenyl-2H-pyrazol-3-yl)-amide;

2-(S)-2-Hydroxy-3-methyl-butylamino)pentanoic acid (5-phenyl-2H-pyrazol-3-yl)-amide;

2-(S)-(7-Methoxy-1,2,3,4-tetrahydro-naphthalen-2-ylamino)-pentanoic acid (5-phenyl-2H-pyrazol-3-yl)-amide;

2-(S)-[(2,3-Dihydro-benzofuran-6-ylmethyl)-amino]-pentanoic acid (5-phenyl-2H-pyrazol-3-yl)-amide;

2-(S)-Decahydro-naphthalen-2-ylamino)-pentanoic acid (5-phenyl-2H-pyrazol-3-yl-amide;

2-(S)-1,2,3,4-Tetrahydro-naphthalen-2-ylamino)-pentanoic acid (5-phenyl-2H-pyrazol-3-yl)amide;

2-(S)-1,2,3,4-Tetrahydro-naphthalen-2-ylamino)-pentanoic acid (5-phenyl-2H-pyrazol-3-yl)-amide;

2-(S)-6-Methoxy-1,2,3,4-tetrahydro-naphthalen-2-ylamino)pentanoic acid (5-phenyl-2H-pyrazol-3-yl)-amide;

2-(S)-6,7-Dimethoxy-1,2,3,4-tetrahydro-naphthalen-2-ylamino)-pentanoic acid (5-phenyl-2H-pyrazol-3-yl)-amide;

2-(S)-4-Phenyl-cyclohexylamino)-pentanoic acid (5-phenyl-2H-pyrazol-3-yl)amide;

2-(S)-6,7,8,9-Tetrahydro-5H-benzocyclohepten-6-ylamino)-pentanoic acid (5-phenyl-2H-pyrazol-3-yl)-amide;

2-(S)-5-Methoxy-1,2,3,4-tetrahydro-naphthalen-2-ylamino)-pentanoic acid (5-phenyl-2H-pyrazol-3-yl)-amide;

2-(S)-3-Fluoro-6,7,8,9-tetrahydro-5H-benzocyclohepten-6-ylamino)-pentanoic acid (5-phenyl-2H-pyrazol-3-yl)-amide;

2-(S)-3-Phenyl-cyclobutylamino)-pentanoic acid (5-phenyl-2H-pyrazol-3-yl)amide;

2-(S)-5-Chloro-indan-2-ylamino)-pentanoic acid (5-phenyl-2H-pyrazol-3-yl)-amide;

2-(S)-7-Nitro-1,2,3,4-tetrahydro-naphthalen-2-ylamino)-pentanoic acid (5-phenyl-2H-pyrazol-3-yl)amide;

2-(S)-5-Fluoro-indan-2-ylamino)-pentanoic acid (5-phenyl-2H-pyrazol-3-yl)-amide;

2-(S)-3,3,5,5-Tetramethyl-cyclohexylamino)-pentanoic acid (5-phenyl-2H-pyrazol-3-yl)-amide;

2-(S)-7-Phenyl-1,2,3,4-tetrahydro-naphthalen-2-ylamino)-pentanoic acid (5-phenyl-2H-pyrazol-3-yl)-amide;

2-(S)-7-Furan-3-yl-1,2,3,4-tetrahydro-naphthalen-2-ylamino)-pentanoic acid (5-phenyl-2H-pyrazol-3-yl)-amide;

2-(S)-[7-(3,5-Dimethyl-phenyl)-1,2,3,4-tetrahydro-naphthalen-2-ylamino]-pentanoic acid (5-phenyl-2H-pyrazol-3-yl)-amide;

2-(S)-3,5-Difluoro-benzylamino)-pentanoic acid (5-phenyl-2H-pyrazol-3-yl)-amide;

2-(S)-[2-(3,5-Difluoro-phenyl)-ethylamino]-pentanoic acid (5-phenyl-2H-pyrazol-3-yl)-amide;

2-(S)-[2-(3,5-Difluoro-phenyl)-ethylamino]-N-(5-phenyl-2H-pyrazol-3-yl)-propionamide; and 2-(S)-Indan-2-ylamino)-N-(5phenyl-2H-pyrazol-3-yl)-propionamide.

As indicated, so-called 'prodrugs' of the compounds of Formula I are also within the scope of the invention. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Some examples of prodrugs in accordance with the invention include, but are not limited to, (i) where the compound of Formula I contains a carboxylic acid functionality (—COOH), an ester thereof, for example, a compound wherein the hydrogen of the carboxylic acid functionality of the compound of Formula (I) is replaced by ($C_1$-$C_8$)alkyl;

(ii) where the compound of Formula I contains an alcohol functionality (—OH), an ether thereof, for example, a compound wherein the hydrogen of the alcohol functionality of the compound of Formula I is replaced by ($C_1$-$C_6$)alkanoyloxymethyl; and (iii) where the compound of Formula I contains a primary or secondary amino functionality (—$NH_2$ or —NHR where R≠H), an amide thereof, for example, a compound wherein, as the case may be, one or both hydrogens of the amino functionality of the compound of Formula I is/are replaced by ($C_1$-$C_{10}$)alkanoyl.

Further examples of replacement groups in accordance with the foregoing examples and examples of other prodrug types may be found in the aforementioned references.

Moreover, certain compounds of Formula I may themselves act as prodrugs of other compounds of Formula I.

Also included within the scope of the invention are metabolites of compounds of Formula I, that is, compounds formed in vivo upon administration of the drug. Some examples of metabolites in accordance with the invention include, but are not limited to, (i) where the compound of Formula I contains a methyl group, an hydroxymethyl derivative thereof (—$CH_3$->—$CH_2OH$):

(ii) where the compound of Formula I contains an alkoxy group, an hydroxy derivative thereof (—OR->—OH);

(iii) where the compound of Formula I contains a tertiary amino group, a secondary amino derivative thereof (—$NR^1R^2$->—$NHR^1$ or —$NHR^2$);

(iv) where the compound of Formula I contains a secondary amino group, a primary derivative thereof (—$NHR^1$->—$NH_2$);

(v) where the compound of Formula I contains a phenyl moiety, a phenol derivative thereof (—Ph->—PhOH); and (vi) where the compound of Formula I contains an amide group, a carboxylic acid derivative thereof (—$CONH_2$->COOH).

Compounds of Formula I containing one or more asymmetric carbon atoms can exist as two or more stereoisomers. Where a compound of Formula I contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of Formula I containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of Formula I, including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

The present invention includes all pharmaceutically acceptable isotopically-labeled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include, but are not limited to, isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labeled compounds of Formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds of Formula II as hereinbefore defined, all salts, solvates and complexes thereof and all solvates and complexes of salts thereof as defined hereinbefore for compounds of Formula I. The invention includes all polymorphs of the aforementioned species and crystal habits thereof.

When preparing compounds of Formula I in accordance with the invention, it is open to a person skilled in the art to routinely select the form of compound of Formula II which provides the best combination of features for this purpose. Such features include, but are not limited to, the melting point, solubility, processability and yield of the intermediate form and the resulting ease with which the product may be purified on isolation.

Compounds of the Formula I of this invention, and their pharmaceutically acceptable salts, have useful pharmaceutical and medicinal properties. The compounds of Formula I, and their pharmaceutically acceptable salts inhibit the production of Aβ-peptide (thus, gamma-secretase activity) in mammals, including humans. Compounds of the Formula I, and their pharmaceutically acceptable salts, are therefore able to function as therapeutic agents in the treatment of the neurodegenerative and/or neurological disorders and diseases enumerated below, for example Alzheimer's disease, in an afflicted mammal, including a human.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome in a mammal, including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or condition selected from the group consisting of Alzheimer's disease and Down's Syndrome in a mammal, including a human, comprising an amount of a compound of the Formula I, or a pharmaceutically acceptable salt thereof, that is effective in inhibiting Aβ-peptide production, and a pharmaceutically acceptable carrier.

The present invention also relates to a pharmaceutical composition for treating a disease or a condition selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome in a mammal, including a human, comprising an amount of a compound of the Formula I, or a pharmaceutically acceptable salt thereof, that is effective in treating such disease or condition, and a pharmaceutically acceptable carrier.

The present invention also relates to a pharmaceutical composition for treating a disease or a condition selected from the group consisting of Alzheimer's disease and Down's Syndrome in a mammal, including a human, comprising an amount of a compound of the Formula I, or a pharmaceutically acceptable salt thereof, that is effective in treating such disease or condition, and a pharmaceutically acceptable carrier.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis and Down's Syndrome in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Aizheimer's disease and Down's Syndrome in a mammal, including a human, comprising administering to said mammal an amount of a compound of the Formula I, or a pharmaceutically acceptable salt thereof, that is effective in inhibiting Aβ-production.

The present invention also relates to a method of treating a disease or condition selected from Alzheimer's disease, hereditary cerebral hemorrhage with amyloidosis, cerebral amyloid angiopathy, a prion-mediated disease, inclusion body myositis, stroke, multiple sclerosis and Down's Syndrome in a mammal, including a human, comprising administering to said mammal an amount of a compound of the Formula I, or a pharmaceutically acceptable salt thereof, that is effective in treating such condition.

The present invention also relates to a method of treating a disease or condition selected from Alzheimer's disease and Down's Syndrome in a mammal, including a human, comprising administering to said mammal an amount of a compound of the Formula I, or a pharmaceutically acceptable salt thereof, that is effective in treating such condition.

Compounds of the Formula I may be used alone or used in combination with any other drug, including, but not limited to, any memory enhancement agent, e.g., Aricept™, antidepressant agent, e.g., Zoloft™, anxiolytic, antipsychotic agent, e.g., Geodon™, sleep disorder agent, anti-inflammatory agent e.g., Celebrex™, Bextra™, etc., anti-oxidant agent, cholesterol modulating agent (for example, an agent that lowers LDL or increases HDL), e.g., Lipitor™, or anti-hypertension agent.

The present invention also relates to a pharmaceutical composition for treating a disease or condition associated with Aβ-peptide production in a mammal, including a human, comprising (a) a compound of the Formula I, or a pharmaceutically acceptable salt thereof; (b) a memory enhancement agent, antidepressant, anxiolytic, antipsychotic agent, sleep disorder agent, anti-inflammatory agent, anti-oxidant agent, cholesterol modulating agent or anti-hypertensive agent; and (c) a pharmaceutically acceptable carrier; wherein the active agents "a" and "b" above are present in amounts that render the composition effective in treating such disease or condition.

The present invention also relates to a pharmaceutical composition for treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome, in a mammal, including a human, comprising (a) a compound of the Formula I, or a pharmaceutically acceptable salt thereof; (b) a memory enhancement agent, antidepressant, anxiolytic, antipsychotic agent, sleep disorder agent, anti-inflammatory agent, anti-oxidant agent, cholesterol modulating agent or anti-hypertensive agent; and (c) a pharmaceutically acceptable carrier; wherein the active agents "a" and "b" above are present in amounts that render the composition effective in treating such disease or condition.

The present invention also relates to a pharmaceutical composition for treating a disease or condition selected from the group consisting of Alzheimer's disease and Down's Syndrome, in a mammal, including a human, comprising (a) a compound of the Formula I, or a pharmaceutically acceptable salt thereof; (b) a memory enhancement agent, antidepressant, anxiolytic, antipsychotic agent, sleep disorder agent, anti-inflammatory agent, anti-oxidant agent, cholesterol modulating agent or anti-hypertensive agent; and (c) a pharmaceutically acceptable carrier; wherein the active agents "a" and "b" above are present in amounts that render the composition effective in treating such disease or condition.

The present invention also relates to a method of treating a disease or condition associated with Aβ-peptide production in a mammal, including a human, comprising administering to said mammal (a) a compound of the Formula I, or a pharmaceutically acceptable salt thereof; and (b) a memory enhancement agent, antidepressant, anxiolytic, antipsychotic agent, sleep disorder agent, anti-inflammatory agent, anti-oxidant agent, cholesterol modulating agent or anti-hypertensive agent; wherein the active agents "a" and "b" above are present in amounts that render the composition effective in treating such disease or condition.

The present invention also relates to a method of treating a disease or condition selected from the group consisting of Alzheimer's disease, hereditary cerebral hemorrhage with amyloidosis, cerebral amyloid angiopathy, a prion-mediated disease, inclusion body myositis, stroke, multiple sclerosis and Down's Syndrome, in a mammal, including a human, comprising administering to said mammal (a) a compound of the Formula I, or a pharmaceutically acceptable salt thereof; and (b) a memory enhancement agent, antidepressant, anxiolytic, antipsychotic agent, sleep disorder agent, anti-inflammatory agent, anti-oxidant agent, cholesterol modulating agent or anti-hypertensive agent; wherein the active agents "a" and "b" above are present in amounts that render the composition effective in treating such disease or condition.

The present invention also relates to a method of treating a disease or condition selected from the group consisting of Alzheimer's disease and Down's Syndrome, in a mammal, including a human, comprising administering to said mammal (a) a compound of the Formula I, or a pharmaceutically acceptable salt thereof; and (b) a memory enhancement agent, antidepressant, anxiolytic, antipsychotic agent, sleep disorder agent, anti-inflammatory agent, anti-oxidant agent, cholesterol modulating agent or anti-hypertensive agent; wherein the active agents "a" and "b" above are present in amounts that render the composition effective in treating such disease or condition.

Compounds of the Formula I, or any of the combinations described in the preceding paragraphs, may optionally be used in conjunction with a know P-glycoprotein inhibitor, such as verapamil.

References herein to diseases and conditions "associated with Aβ-peptide production" relate to diseases or conditions that are caused, at least in part, by Aβ-peptide and/or the production thereof. Thus, Aβ-peptide is a contributing factor, but not necessarily the only contributing factor, to "a disease or condition associated with Aβ-peptide production."

The compounds of Formula I, or their pharmaceutically acceptable salts may also be used to modulate or inhibit the Notch signaling pathway in organisms, including humans. The Notch signaling pathway is an evolutionarily conserved mechanism utilized by organisms, ranging from worms through humans, to regulate fate determination of various cell lineages. Notch belongs to the family of epidermal growth factor-like homeotic genes, which encode transmembrane proteins with variable numbers of epidermal growth factor-like repeats in the extracellular domain. There is increasing evidence for a role of the Notch pathway in human disease. All of the components of the pathway have yet to be identified, but among those identified to date, mutations that affect their interaction with each other can lead to a variety of syndromes and pathological conditions.

For example, Notch signaling is typically associated with cell fate decision. The finding that Notch activation stimulates capillary outgrowth suggests that Notch receptors must be activated to allow this process to occur. Therefore, Notch modulation provides a method for regulating angiogenesis. Specifically, modulation of Notch signaling can be used to modulate angiogenesis (e.g., by blocking Notch signaling to block angiogenesis). This inhibition of angiogenesis in vivo can be used as a therapeutic means to treat a variety of diseases, including but not limited to cancer, diabetic retinopathy, rheumatoid arthritis, psoriasis, inflammatory bowel disease and arteriosclerosis.

The Notch pathway is also implicated in the development and maturation of T cells, as described in Radtke, F. et al., Immunity 10:547-558, 1999. The compounds of Formula I, and their pharmaceutically acceptable salts are therefore useful candidates for modulating the immune system, including the treatment of inflammation, asthma, graft rejection, graft versus host disease, autoimmune disease and transplant rejection.

In addition, a number of studies published between 2002 and 2004 have provided convincing evidence that Notch signaling is frequently elevated in a variety of human tumors (including, but not limited to breast, prostate, pancreas and T-cell acute lymphoblastic leukemia). One key study provides a strong genetic link to Notch's role in important tumor types. Specifically, Weijzen et al. demonstrated that Notch signaling maintains the neoplastic phenotype in human Ras-transformed cells. Weijzen et al. (2002) *Nature Med* 8: 979. Because 30% of human malignancies may carry activating mutations in at least one of the three isoforms of Ras, this finding raises the possibility that Notch inhibitors would be a powerful addition to anti-cancer therapy. Another study's findings support a central role for aberrant Notch signaling in the pathogenesis of human T cell acute lymphoblastic leukemia/lymphoma. Pear et al., *Current Opinion in Hematology* (2004), 11(6), 426-433.

Accordingly, the compounds of Formula I, and their pharmaceutically acceptable salts, may be used for treating a disease or condition selected from the group consisting of cancer, arteriosclerosis, diabetic retinopathy, rheumatoid arthritis, psoriasis, inflammatory bowel disease inflammation, asthma, graft rejection, graft versus host disease, autoimmune disease and transplant rejection.

As used herein, the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

DETAILED DESCRIPTION OF THE INVENTION

Compounds of the Formula I, and their pharmaceutically acceptable salts, may be prepared as described in the following reaction Schemes and discussion. Unless otherwise indicated, as referred to in the reaction schemes and discussion that follow, $R^1$, $R^{1a}$, $R^{1b}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and n are as defined above.

The compounds of Formula I may have asymmetric carbon atoms and may therefore exist as racemic mixtures, diastereoisomers, or as individual optical isomers.

Separation of a mixture of isomers of compounds of Formula I into single isomers may be accomplished according to conventional methods known in the art. Enantiomers or diasteroisomers may be separated by chiral column chromatography, or separated through recrystallization of the corresponding salt prepared by addition of an appropriate chiral acid or base.

The compounds of the Formula I may be prepared by the methods described below, together with synthetic methods known in the art of organic chemistry, or modifications and derivatisations that are familiar to those of ordinary skill in the art. Preferred methods include, but are not limited to, those described below.

The reactions described below are performed in solvents that are appropriate to the reagents and materials employed and that are suitable for use in the reactions described. In the description of the synthetic methods described below, it is also to be understood that all reaction conditions, whether actual or proposed, including choice of solvent, reaction temperature, reaction duration time, reaction pressure, and other reaction conditions (such as anhydrous conditions, under argon, under nitrogen, etc.), and work up procedures, are those conditions that are standard for that reaction, as would be readily recognized by one of skill in the art. Alternate methods may also be used.

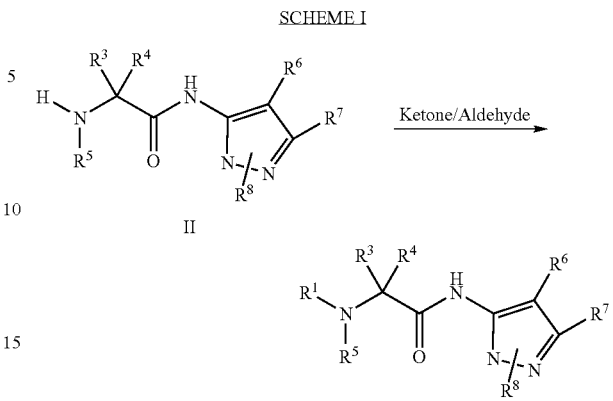

SCHEME I

Referring to Scheme 1, compounds of formula I wherein $R^1$ is —$C_1$-$C_{20}$ alkyl, —$C_2$-$C_{20}$ alkenyl, —$C_2$-$C_{20}$ alkynyl, —$C_3$-$C_8$ cycloalkyl, —$C_5$-$C_8$ cycloalkenyl, —($C_5$-$C_{11}$)bi- or tricycloalkyl, —($C_7$-$C_{11}$)bi- or tricycloalkenyl, -(3-8 membered) heterocycloalkyl, -(5-11 membered) heterobicycloalky or $R^5$ is $C_1$-$C_6$ alkyl, it can be prepared by using a well-established reductive amination method by reacting compounds in formula II with a ketone or aldehyde with or without acid catalyst (such as acetic acid), ammonium acetate/dry agents (such as anhydrous $Na_2SO_4$ or $MgSO_4$), and a reducing agent such as sodium triacetoxy borohydride (NaBH(OAc)$_3$), sodium cyanoborohydride (NaCNBH$_3$), sodium borohydride, or the corresponding polymer bound-NaBH4, polymer bound-NaCNBH$_3$, polymer bound-NaBH (OAc)$_3$, or any reducing agent (e.g., hydrogenation) that is known in the literature for reducing the imine bond to the corresponding amine in an appropriate solvent, such as dichloroethane, chloroform, THF, MeOH, ethanol, about isopropanol, t-butanol or toluene, at a temperature between room temperature to reflux, preferably at about room temperature to about 65° C. (For review, see, Baxter, Ellen W.; Reitz, Allen B. Organic Reactions (New York) (2002), 59 1-714; Tarasevich, Vladimir A.; Kozlov, Nikolai G. Russian Chemical Reviews (1999), 68(1), 55-72.) Alternatively, it can be prepared by well-established alkylation method by reacting compound of formula II with an alkyl-$L_1$ wherein $L_1$ is a leaving group, such as a halide (I, Br, Cl) or tosylate (OTs), myslate (OMs), trifilate (OTf) in the presence of an appropriate base selecting from a tertiary amine (e.g., triethylamine, diisopropylamine, dimethylaminopyridine, sodium hydroxide, potassium carbonate, cesium carbonate) in an appropriate solvenet selecting from C1-C4 alcohol, THF, methylene chloride, dichloroethane, dimethylformamide, DMSO, pyridine, N-methylpyrrolidone, toluene, xylene, acetonitrile, acetone, proprionitrile at an appropriate temperature form room temperature to refluxing.

Compounds of formula I wherein $R^1$ is —$C_6$-$C_{14}$ aryl and -(5-15 membered) heteroaryl, it can be prepared by reacting compound of formula II with aryl-$L_1$ or heteroaryl-L1, or well-established Pd-catalyzed amination (References: J. Org. Chem., 2000, 65, 1158), wherein $L_1$ is a leaving group, such as a halide (I, Br, Cl) or tosylate (OTs), myslate (OMs), trifilate (OTf) in the presence of an appropriate base selecting from a tertiary amine (e.g., triethylamine, diisopropylamine, dimethylaminopyridine, sodium hydroxide, potassium carbonate, cesium carbonate, potassium or sodium alkoxide (t-butoxide, methoxide), potassium or sodium hydride, with or without an organometallics (e.g., Pd(OAc)$_2$, Pd(dba)$_2$, Pd(PPh$_3$)$_4$ and a ligand such as PPh$_3$, BINAP, PPh$_3$ PCy$_3$, P(t-Bu)$_3$, and related ligand know in literature in an appropriate solvent selecting from $C_1$-$C_4$ alcohol, THF, methylene chloride, dichloroethane, dimethylformamide, DMSO, N-methylpyrrolidone, xylene, toluene, acetonitrile, pyridine, acetone, proprionitrile at an appropriate temperature form room temperature to refluxing;

Compounds of formula II in turn can be synthesized by reacting 3-amino pyrazole (Commercially available or prepared using known literature methods. Reference: G. F. Duffin, J. D. Kendall, J. Chem. Soc. 1954, 408; W. E. Parham, J. L. Bleasdale, J. Am. Chem. Soc., 1951, 4664; H. Lund, J. Chem. Soc. 1933, 686; G. Ege, H. Franz, J. Heterocycle Chem., 1982, 1267; C. N. Kirsten, T. H. Schrader, J. Am. Chem. Soc. 1997, 12061) with N-protected amino acids using the standard coupling methods such as carbodiimide, i.e. 1,3-dicyclohexylcarbodiimide (DCC), 1,3-diisopropylcarbodiimide, 1-(3-dimethylaminopropyl)-3-ethylcarbodiimide (EDAC or EDCI), O-(1,2-dihydro-2-oxo-1-pyridyl)N,N,N', N'-tetramethyluronium tetrafluoroborate (TPTU), 2-(1H-benzotriazole-1-yl)-1,1,3,3-tetramethyluronium tetrafluoroborate (TBTU), N-cyclohexylcarbodiimide, or N'-methylpolystyrene in the presence or absence of 1-hydroxy-benzotriazole (HOBt), in a suitable solvent such as dichloromethane (CH2Cl2), chloroform (CHCl3), tetrahydrofuran (THF), diethyl ether (Et2O), 1,4-dioxane, acetonitrile (CH3CN), toluene, N,N-dimethylformamide (DMF) followed by thermal rearrangement carried out in an appropriate solvent such as toluene at elevated temperature, preferably from 100° C. to 200° C. Compounds of Formula II can then be obtained by removing the N-protecting group: strong acid in the case of t-butoxycarbonyl or through hydrogenolysis in the case of carbobenzyloxycarbonyl.

The starting materials used in the procedures of the above Schemes, the syntheses of which are not described above, are either commercially available, known in the art or readily obtainable from known compounds using methods that will be apparent to those skilled in the art. (e.g., WO2004/033434).

Alternatively, compounds in formula I may be prepared from left to right as shown in Scheme II using the methods analogous to that described in Scheme I.

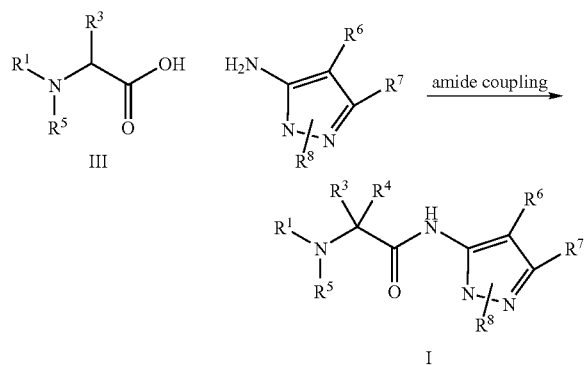

SCHEME II

The starting materials used in the procedure of the above Scheme II, the syntheses of which are not described above, are either commercially available, known in the art or readily obtainable from known compounds using methods that will be apparent to those skilled in the art.

The compounds of Formula I, and the intermediates shown in the above reaction schemes, may be isolated and purified by conventional procedures, such as recrystallization or chromatographic separation, such as on silica gel, either with an ethyl acetate/hexane elution gradient, a methylene chloride/methanol elution gradient, or a chloroform/methanol elution gradient. Alternatively, a reverse phase preparative HPLC or chiral HPLC separation technique may be used.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

Pharmaceutically acceptable salts of the compounds of Formula I may be prepared in a conventional manner by treating a solution or suspension of the corresponding free base or acid with one chemical equivalent of a pharmaceutically acceptable acid or base. Conventional concentration or crystallization techniques may be employed to isolate the salts. Suitable acids, include, but are not limited to, acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic and related acids. Suitable bases include, but are not limited to, sodium, potassium and calcium.

A compound of the Formula I of the present invention may be administered to mammals via either the oral, parenteral (such as subcutaneous, intravenous, intramuscular, intrasternal and infusion techniques), rectal, intranasal, topical or transdermal (e.g., through the use of a patch) routes. In general, these compounds are most desirably administered in doses ranging from about 0.1 mg to about 1000 mg per day, in single or divided doses (i.e., from 1 to 4 doses per day), although variations will necessarily occur depending upon the species, weight, age and condition of the subject being treated, as well as the particular route of administration chosen. However, a dosage level that is in the range of about 0.1 mg/kg to about 5 gm/kg body weight per day, preferably from about 0.1 mg/kg to about 100 mg/kg body weight per day, is most desirably employed. Nevertheless, variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such higher dosage levels are first divided into several small doses for administration throughout the day.

A compound of the Formula I of the present invention may be administered alone or in combination with pharmaceutically acceptable carriers or diluents by either of the routes previously indicated, and such administration may be carried out in single or multiple doses. Suitable pharmaceutical carriers include solid diluents or fillers, sterile aqueous media and various non-toxic organic solvents, etc. The pharmaceutical compositions formed by combining a compound of the Formula I, or a pharmaceutically acceptable salt thereof, with a pharmaceutically acceptable inert carrier, can then be readily administered in a variety of dosage forms such as tablets, capsules, lozenges, troches, hard candies, powders, sprays, creams, salves, suppositories, jellies, gels, pastes, lotions, ointments, aqueous suspensions, injectable solutions, elixirs, syrups, and the like. Moreover, oral pharmaceutical compositions may be suitably sweetened and/or flavored.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), methylcellulose, alginic acid and certain complex silicates, together with granulation binders such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions containing a compound of the Formula I of the present invention in either sesame or peanut oil or in aqueous propylene glycol may be employed. The aqueous solutions should be suitably buffered (preferably pH greater than 8) if necessary and the liquid diluent first rendered isotonic with sufficient saline or glucose. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The compounds of Formula I of the present invention are useful in inhibiting Aβ-peptide production (thus, gamma-secretase activity) in mammals, and therefore they are able to function as therapeutic agents in the treatment of the aforementioned disorders and diseases in an afflicted mammal.

The ability of compounds of the Formula I of this invention, and their pharmaceutically acceptable salts, to inhibit Aβ-peptide production (thus, gamma-secretase activity) may be determined using biological assays known to those of ordinary skill in the art, for example the assays described below.

The activity of compounds of the Formula I of the present invention in inhibiting gamma-secretase activity is determinable in a solubilized membrane preparation generally according to the description provided in McLendon et al. Cell-free assays for γ-secretase activity, The FASEB Journal (Vol. 14, December 2000, pp. 2383-2386). Compounds of the present invention were determined to have an $IC_{50}$ activity for inhibiting gamma-secretase activity of less than about 100 micromolar.

The following Examples illustrate the present invention. It is to be understood, however, that the invention, as fully described herein and as recited in the claims, is not intended to be limited by the details of the following Examples.

EXPERIMENTAL PROCEDURES

General Procedure for Reductive Amination:
Sodium Triacetoxyborohydride

An amine (14 eq.) in dichloromethane, dichloroethane or THF was added to a solution of a ketone or aldehyde (1 eq.), NaBH(OAc)₃ (1-3 eq.) and acetic acid (1-3 eq.) in dichloromethane, dichloroethane or THF. The mixture was stirred at room temperature until product formation or disappearance of the starting material. The mixture was quenched with diluted base, extracted with methylene chloride or other appropriate solvent such as chloroform or ethyl acetate. The organic layer was separated, dried and concentrated to give the desired amine. Purification may be necessary.

Sodium Cyanoborohydride

A mixture of a ketone or aldehyde (1 eq.), an amine (1-4 eq.), sodium cyanoborohydride (1-5 eq.), with catalytic amount of zinc chloride in an appropriate solvent such as Methanol, or THF was stirred at room temperature to 60° C. until product formation or disappearance of the starting material. The mixture was quenched with diluted base, extracted with methylene chloride or other appropriate solvent such as chloroform or ethyl acetate. The organic layer was separated, dried and concentrated to give the desired amine. Purification may be necessary.

Example 1

2(S)-[2-(2,3-Difluoro-phenyl)-ethylamino]-pentanoic acid (5-phenyl-2H-pyrazol-3-yl)-amide 3-amino-5-phenyl pyrazole (31.2 mmol) was combined with (S)-2-tert-butoxycarbonylamino-pentanoic acid (37.5 mmol) and dissolved in 50 mL of anhydrous dichloromethane. Triethylamine (93.6 mmol) was added, followed by TBTU (37.5 mmol) and the reaction mixture was stirred at rt for 2 h. The solution was then diluted with 50 mL of fresh dichloromethane and extracted with 50 mL portions of aqueous saturated bicarbonate solution, water and then brine. The organics were dried over Na₂SO₄, filtered and concentrated under reduced pressure. The residue was purified through flash chromatography on silica gel. The purified product was then heated neat at 150° C. for 3 h. The reaction mixture (14.4 mmol) was then cooled to rt and dissolved in 40 mL of anhydrous 4.0 N HCl dioxane solution and stirred at rt for 3 h. The reactions were concentrated under reduced pressure and triturated with 20 mL of anhydrous Et₂O. The solids were filtered and dried to give the desired amine, (S)-2-Amino-pentanoic acid (5-phenyl-2H-pyrazol-3-yl)-amide. 2-(2,3-Difluoro-phenyl)-acetaldehyde (0.2 mmol) was combined with (S)-2-Amino-pentanoic acid (5-phenyl-2H-pyrazol-3-yl)-amide (0.2 mmol) in 2 mL of anhydrous dichloromethane under N₂. Sodium triacetoxyborohydride (0.3 mmol) and two drops of acetic acid were then added and the reaction was stirred at rt for 16 h. The crude solution was then concentrated under reduced pressure and purified through flash chromatography on silica gel to give 2-(S)-[2-(2,3-Difluoro-phenyl) ethylamino]-pentanoic acid (5-phenyl-2H-pyrazol-3-yl)-amide, LC-MS 2.7 min, 398 [M+1].

The following Examples in Table 1 were synthesized by methods analogous to those described above.

TABLE 1

| Example | Name | MS |
|---|---|---|
| 2 | 2-(S)-Cyclohexylmethyl-amino)-pentanoic acid (5-phenyl-2H-pyrazol-3-yl)-amide | LC-MS 3.4 min, 355 [M + 1] |
| 3 | 2-(S)-Indan-2-ylamino)-pentanoic acid (5-phenyl-2H-pyrazol-3-yl)-amide | LC-MS 1.7 min, 375 [M + 1] |
| 4 | 2-(S)-1,2,3,4-Tetrahydro-naphthalen-2-ylamino)-pentanoic acid (5-phenyl-2H-pyrazol-3-yl)-amide | LC-MS 1.8 min, 389 [M + 1] |
| 5 | 2-(S)-2-Hydroxy-2-phenyl-ethylamino)-pentanoic acid (5-phenyl-2H-pyrazol-3-yl)-amide | APCI 379/377 [M + 1] |
| 6 | 2-(S)-2-Cyclohexyl-2-hydroxy-ethylamino)-pentanoic acid (5-phenyl-2H-pyrazol-3-yl)-amide | LC-MS 1.9 min, 385 [M + 1] |

TABLE 1-continued

| Example | Name | MS |
|---|---|---|
| 7 | 2-(S)-Indan-1-ylamino)-pentanoic acid (5-phenyl-2H-pyrazol-3-yl)-amide | LC-MS 1.7 min, 375 [M + 1] |
| 8 | 2-(S)-5-Fluoro-indan-1-ylamino)-pentanoic acid (5-phenyl-2H-pyrazol-3-yl)-amide | APCI 393/391 [M + 1] |
| 9 | 2-(S)-6-Bromo-1,2,3,4-tetrahydro-naphthalen-2-ylamino)-pentanoic acid (5-phenyl-2H-pyrazol-3-yl)-amide | APCI 468/466 [M + 1] |
| 10 | 2-(S)-3-Phenyl-indan-1-ylamino)-pentanoic acid (5-phenyl-2H-pyrazol-3-yl)-amide | LC-MS 2.1 min, 451 [M + 1] |
| 11 | 2-(S-)2-Hydroxy-3-methyl-butylamino)-pentanoic acid (5-phenyl-2H-pyrazol-3-yl)-amide | APCI 345/343 [M + 1] |
| 12 | 2-(S)-7-Methoxy-1,2,3,4-tetrahydro-naphthalen-2-ylamino)-pentanoic acid (5-phenyl-2H-pyrazol-3-yl)-amide | LC-MS 1.9 min, 419 [M + 1] |
| 13 | 2-(S)-[(2,3-Dihydro-benzofuran-6-ylmethyl)-amino]-pentanoic acid (5-phenyl-2H-pyrazol-3-yl)-amide | LC-MS 1.7 min, 391 [M + 1] |
| 14 | 2-(S)-Decahydro-naphthalen-2-ylamino)-pentanoic acid (5-phenyl-2H-pyrazol-3-yl)-amide | LC-MS 1.9 min, 395 [M + 1] |
| 15 | 2-(S)-1,2,3,4-Tetrahydro-naphthalen-2-ylamino)-pentanoic acid (5-phenyl-2H-pyrazol-3-yl)-amide | LC-MS 1.9 min, 389 [M + 1] |
| 16 | 2-(S)-1,2,3,4-Tetrahydro-naphthalen-2-ylamino)-pentanoic acid (5-phenyl-2H-pyrazol-3-yl)-amide | LC-MS 1.9 min, 389 [M + 1] |
| 17 | 2-(S)-6-Methoxy-1,2,3,4-tetrahydro-naphthalen-2-ylamino)-pentanoic acid (5-phenyl-2H-pyrazol-3-yl)-amide | LC-MS 2.0 min, 419 [M + 1] |
| 18 | 2-(S)-6,7-Dimethoxy-1,2,3,4-tetrahydro-naphthalen-2-ylamino)-pentanoic acid (5-phenyl-2H-pyrazol-3-yl)-amide | LC-MS 1.3 min, 449 [M + 1] |
| 20 | 2-(S)-4-Phenyl-cyclohexylamino)-pentanoic acid (5-phenyl-2H-pyrazol-3-yl)-amide | LC-MS 2.1 min, 417 [M + 1] |
| 21 | 2-(S)-6,7,8,9-Tetrahydro-5H-benzocyclohepten-6-ylamino)-pentanoic acid (5-phenyl-2H-pyrazol-3-yl)-amide | LC-MS 2.0 min, 403 [M + 1] |
| 22 | 2-(S)-5-Methoxy-1,2,3,4-tetrahydro-naphthalen-2-ylamino)-pentanoic acid (5-phenyl-2H-pyrazol-3-yl)-amide | LC-MS 2.0 min, 419 [M + 1] |
| 23 | 2-(S)-3-Fluoro-6,7,8,9-tetrahydro-5H-benzocyclohepten-6-ylamino)-pentanoic acid (5-phenyl-2H-pyrazol-3-yl)-amide | APCI 421 [M + 1] |
| 24 | 2-(S)-3-Phenyl-cyclobutylamino)-pentanoic acid (5-phenyl-2H-pyrazol-3-yl)-amide | LC-MS 1.8 min, 389 [M + 1] |
| 25 | 2-(S)-5-Chloro-indan-2-ylamino)-pentanoic acid (5-phenyl-2H-pyrazol-3-yl)-amide | APCI 409/407 [M + 1] |
| 26 | 2-(S)-7-Nitro-1,2,3,4-tetrahydro-naphthalen-2-ylamino)-pentanoic acid (5-phenyl-2H-pyrazol-3-yl)-amide | LC-MS 1.8 min, 436 [M + 1] |
| 27 | 2-(S)-5-Fluoro-indan-2-ylamino)-pentanoic acid (5-phenyl-2H-pyrazol-3-yl)-amide | LC-MS 1.8 min, 393 [M + 1] |
| 30 | 2-(S)-3,3,5,5-Tetramethyl-cyclohexylamino)-pentanoic acid (5-phenyl-2H-pyrazol-3-yl)-amide | LC-MS 1.8 min, 397 [M + 1] |
| 31 | 2-(S)-7-Phenyl-1,2,3,4-tetrahydro-naphthalen-2-ylamino)-pentanoic acid (5-phenyl-2H-pyrazol-3-yl)-amide | LC-MS 2.3 min, 465 [M + 1] |
| 32 | 2-(S)-7-Furan-3-yl-1,2,3,4-tetrahydro-naphthalen-2-ylamino)-pentanoic acid (5-phenyl-2H-pyrazol-3-yl)-amide | LC-MS 2.0 min, 455 [M + 1] |
| 33 | 2-(S)-[7-(3,5-Dimethyl-phenyl)-1,2,3,4-tetrahydro-naphthalen-2-ylamino]-pentanoic acid (5-phenyl-2H- | LC-MS 2.4 min, 493 [M + 1] |
| 35 | 2-(S)-3,5-Difluoro-benzylamino)-pentanoic acid (5-phenyl-2H-pyrazol-3-yl)-amide | APCI 385/383 [M + 1] |
| 36 | 2-(S)-[2-(3,5-Difluoro-phenyl)-ethylamino]-pentanoic acid (5-phenyl-2H-pyrazol-3-yl)-amide | LC-MS 0.2 min, 397 [M + 1] |
| 38 | 2-(S)-[2-(3,5-Difluoro-phenyl)-ethylamino]-N-(5-phenyl-2H-pyrazol-3-yl)-propionamide | LC-MS 0.2 min, 369 [M + 1] |
| 39 | 2-(S)-Indan-2-ylamino)-N-(5-phenyl-2H-pyrazol-3-yl)-propionamide | APCI 347/345 [M + 1] |

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:
1. A compound of Formula 1

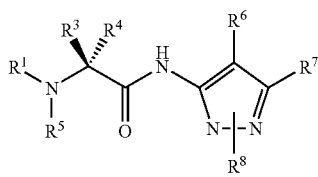

wherein:
R$^1$ is selected from —C$_1$-C$_{20}$ alkyl, —C$_2$-C$_{20}$ alkenyl, —C$_2$-C$_{20}$ alkynyl, —C$_3$-C$_8$ cycloalkyl, —C$_4$-C$_8$ cycloalkenyl, —(C$_5$-C$_{11}$)bi- or tricycloalkyl, —(C$_7$-C$_{11}$)bi- or tricycloalkenyl, -(3-8 membered) heterocycloalkyl, -(5-11 membered) heterobicycloalkyl, —C$_6$-C$_{14}$ aryl and -(5-14 membered) heteroaryl, wherein each hydrogen atom of said alkyl, alkenyl and alkynl of R$^1$ is optionally independently replaced with a —F;

and wherein when R$^1$ is alkyl, alkenyl or alkynyl, R$^1$ is optionally independently substituted with from one to three substituents R$^{1a}$, and wherein when R$^1$ is cycloalkyl, cycloalkenyl, bi- or tricycloalkyl, bi- or tricycloalkenyl, heterocycloalkyl, aryl or heteroaryl, R$^1$ is optionally independently substituted with from one to three substituents R$^{1b}$;

R$^{1a}$ is in each instance independently selected from —C$_1$-C$_6$ alkyl, —C$_2$-C$_6$ alkenyl, —C$_2$-C$_6$ alkynyl, —C$_1$-C$_6$ alkoxy, —C$_2$-C$_6$ alkenoxy, —C$_2$-C$_6$ alkynoxy, —Cl, —Br, —I, —OH, —CN, —NO$_2$, —NR$^9$R$^{10}$, —C(=O)NR$^9$R$^{10}$, —S(O)$_2$NR$^9$R$^{10}$, —C(=O)R$^{11}$, —S(O)$_n$R$^{11}$, —C(=O)OR$^{12}$, —C$_3$-C$_8$ cycloalkyl, —C$_4$-C$_8$ cycloalkenyl, —(C$_5$-C$_{11}$)bi- or tricycloalkyl, —(C$_7$-C$_{11}$)bi- or tricycloalkenyl, -(3-8 membered) heterocycloalkyl, —C$_6$-C$_{14}$ aryl, -(5-14 membered) heteroaryl, —C$_6$-C$_{14}$ aryloxy and -(5-14 membered) heteroaryloxy, wherein said alkyl, alkenyl, alkynyl, alkoxy, alkenoxy, alkynoxy, cycloalkyl, cycloalkenyl, bi- or tricycloalkyl, bi- or tricycloalkenyl, heterocycloalkyl, aryl, heteroaryl, aryloxy and heteroaryloxy of R$^{1a}$ are each optionally independently substituted with from one to three substituents R$^{1b}$;

R$^{1b}$ is in each instance independently selected from —C$_1$-C$_6$ alkyl, —C$_2$-C$_6$ alkenyl, —C$_2$-C$_6$ alkynyl, —C$_1$-C$_6$ alkoxy, —C$_2$-C$_6$ alkenoxy, —C$_2$-C$_6$ alkynoxy, —F, —Cl, —Br, —I, —CN, —NO$_2$, —(C$_{zero}$-C$_4$ alkylene)-NR$^9$R$^{10}$, —(C$_{zero}$-C$_4$ alkylene)-C(=O)NR$^9$R$^{10}$, —(C$_{zero}$-C$_4$ alkylene)-C(=O)R$^{11}$, —(C$_{zero}$-C$_4$ alkylene)-C(=O)OR$^{12}$, —(C$_{zero}$-C$_4$ alkylene)-S(O)$_n$R$^{11}$, —(C$_{zero}$-C$_4$ alkylene)-S(O)$_2$NR$^9$R$^{10}$, —(C$_{zero}$-C$_4$ alkylene)-OH, —C$_1$-C$_6$ hydroxyalkyl, —C$_6$-C$_{14}$ aryl, -(5-15 membered) heteroaryl, —C$_6$-C$_{14}$ aryloxy and -(5-14 membered) heteroaryloxy, wherein said alkyl, alkenyl and alkynyl of R$^{1b}$ are each optionally independently substituted with from one to six substituents independently selected from —F, —Cl, —Br and —I;

R$_3$ is selected from methyl, ethyl, n-propyl, n-butyl, i-butyl, s-butyl, allyl and —CH$_2$CH$_2$SCH$_3$;

R$^4$ is —H, —F or —C$_1$-C$_4$ alkyl;

R$^5$ is selected from —H, —C$_1$-C$_6$ alkyl and —C$_6$-C$_{10}$ aryl, wherein said alkyl and aryl of R$^5$ are each optionally independently substituted with from one to three substituents R$^{1a}$;

or R$^5$ and R$^1$ together with the nitrogen atom to which they are both attached may optionally form a -(5-8 membered) heterocycloalkyl, -(5-8 membered) heterocycloalkenyl or (5-14 membered) heteroaryl, wherein said heterocycloalkyl, heterocycloalkenyl and heteroaryl optionally contains one or two further heteroatoms selected from N, O, and S, and wherein said heterocycloalkyl, heterocycloalkenyl and heteroaryl is optionally independently substituted with from one to three substituents R$^{1b}$;

R$^6$ is selected from —H, —C$_1$-C$_{20}$ alkyl, —Cl, —F, —Br, —I, —CN, —CF$_3$, —C(=O)OR$^{12}$, —S(O)$_2$NR$^9$R$^{10}$, —S(O)$_n$R$^{11}$, —C(=NR$^9$)R$^{15}$, —C$_3$-C$_{12}$ cycloalkyl, —C$_4$-C$_{12}$ cycloalkenyl, and —C$_6$-C$_{10}$ aryl, wherein said alkyl, cycloalkyl, cycloalkenyl and aryl of R$^6$ are each optionally independently substituted with from one to three substituents R$^{1b}$;

R$^7$ is selected from —H, —C$_1$-C$_{12}$ alkyl, —C$_2$-C$_{12}$ alkenyl, —C$_1$-C$_{20}$ alkoxy, C$_2$-C$_{20}$ alkenoxy, —F, Cl, —Br, —I, —CN, —NO$_2$, —C$_3$-C$_{12}$ cycloalkyl, -(3-12 membered) heterocycloalkyl, —C$_6$-C$_{14}$ aryl, -(5-15 membered) heteroaryl, —CHO, —C(=O)(C$_1$-C$_{15}$ alkyl), —C(=O)(5-12 membered)heterocycloalkyl), —C(=O)(C$_6$-C$_{14}$ aryl), —C(=O)(5-15 membered)heteroaryl), —C(O)(C$_5$-C$_{12}$ cycloalkyl), —C(=O)O(C$_1$-C$_8$ alkyl), —C(=O)N(C$_1$-C$_{10}$ alkyl)(C$_1$-C$_{10}$ alkyl), —C(=O)N(C$_1$-C$_{10}$ alkyl)(C$_6$-C$_{10}$ aryl), —C(=O)NH(C$_6$-C$_{10}$ aryl), —C(=O)N(C$_1$-C$_{10}$ alkyl)((5-10 membered) heteroaryl), —C(=O)NH((5-10 membered) heteroaryl), —C(=O)N(C$_1$-C$_{10}$ alkyl)((5-10 membered) heterocycloalkyl), —C(=O)NH((5-10 membered) heterocycloalkyl), —C(=O)N(C$_1$-C$_{10}$ alkyl)(C$_5$-C$_{10}$ cycloalkyl, —C(=O)NH(C$_5$-C$_{10}$ cycloalkyl), —S(O)$_s$(C$_1$-C$_{15}$ alkyl), —S(O)$_s$(C$_5$-C$_{12}$ cycloalkyl), —S(O)$_s$(C$_6$-C$_{15}$ aryl) and —S(O)$_s$((5-10 membered) heteroaryl), wherein each hydrogen atom of said alkyl, alkenyl, alkoxy and alkenoxy of R$^7$ is optionally independently replaced with a —F, and wherein said cycloalkyl and heterocycloalkyl of R$^7$ are each optionally independently substituted with from one to six —F, and wherein said alkyl, alkenyl, cycloalkyl, hetercycloalkyl, aryl and heteroaryl of R$^7$ are each optionally independently substituted with from one to three substituents independently selected from —C$_1$-C$_6$ alkoxy, —C$_2$-C$_6$ alkenoxy, —C$_2$-C$_6$ alkynoxy, —F, —Cl, —Br, —I, —OH, —NR$^9$R$^{10}$, —(CH$_2$)$_{1-10}$NR$^9$R$^{10}$, —C(=O)R$^{11}$, —S(O)OR$^{11}$, —C(=O)NR$^9$R$^{10}$, —S(O)$_2$NR$^9$R$^{10}$, —C$_3$-C$_{12}$ cycloalkyl, -(4-12 membered) heterocycloalkyl, —C$_6$-C$_{15}$ aryl, -(5-15 membered) heteroaryl, —C$_6$-C$_{12}$ aryloxy and -(6-12 membered) heteroaryloxy;

or R$^6$ and R$^7$ together with the carbon atoms to which they are respectively attached may optionally form a —C$_6$-C$_{10}$ aryl, —C$_6$-C$_8$ cycloalkyl, —C$_6$-C$_8$ cycloalkenyl, -(5-8 membered) heterocycloalkyl, -(5-8 membered) heterocycloalkenyl, —C$_{10}$-C$_{14}$ bicycloalkyl, —C$_{10}$-C$_{14}$ bicycloalkenyl, -(10-14 membered) bicycloheteroalkyl or -(10-14 membered) bicycloheteroalkenyl fused to the pyrazole ring of Formula I, wherein said heterocycloalkyl and heterocycloalkenyl each independently contain from one to three heteroatoms independently selected from N, O and S, and wherein said bicycloheteroalkyl and bicycloheteroalkenyl each independently contain from one to five heteroatoms selected independently from N, O and S, and wherein said cycloalkyl, cycloalkenyl, heterocycloalkyl, heterocycloalkenyl, bicycloalkyl, bicycloalkenyl, bicycloheteroalkyl, bicycloheteroalkenyl and aryl are each optionally independently substituted with from one to three substituents $R^{1b}$;

or $R^7$ together with the carbon atom to which it is attached and together with the nitrogen atom of the pyrazole ring of Formula I adjacent to said carbon atom to which $R^7$ is attached may optionally form a -(5-8 membered) heterocycloalkyl, -(5-8 membered) heterocycloalkenyl, -(10-14 membered) bicycloheteroalkyl or -(10-14 membered) bicycloheteroalkenyl fused to the pyrazole ring of Formula I, wherein said heterocycloalkyl and heterocycloalkenyl each independently contain from one to three heteroatoms independently selected from N, O and S, and wherein said bicycloheteroalkyl and bicycloheteroalkenyl each independently contain from one to five heteroatoms independently selected from N, O and S, and wherein said heterocycloalkyl, heterocycloalkenyl, bicycloheteroalkyl and bicycloheteroalkenyl are each optionally independently substituted with from one to three substituents $R^{1b}$;

$R^8$ is selected from —H, —$C_1$-$C_4$ alkyl, —$CF_3$, —C(=O)$R^{11}$, and —C(=O)O$R^{12}$ with the proviso that the pyrazole ring of Formula I is always aromatic and that $R^8$ is attached to either nitrogen in the pyrazole ring of Formula I;

$R^9$ and $R^{10}$ are each independently selected from —H, —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —OH, —C(=O)$R^{11}$, —S(O)$_n$$R^{11}$, —C(=O)O$R^{12}$, —S(O)$_2$N$R^{11}$$R^{12}$, —($C_{zero}$-$C_4$ alkylene)-($C_3$-$C_8$ cycloalkyl), —($C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), —($C_{zero}$-$C_4$ alkylene)-(($C_7$-$C_{11}$)bi- or tricycloalkenyl), —($C_{zero}$-$C_4$ alkylene)-((3-8 membered) heterocycloalkyl), —($C_{zero}$-$C_4$ alkylene)-($C_6$-$C_{14}$ aryl) and —($C_{zero}$-$C_4$ alkylene)-((5-14 membered) heteroaryl), wherein each hydrogen atom of said alkyl, alkenyl, alkynyl, alkoxy, alkenoxy and alkynoxy of $R^9$ and $R^{10}$ is optionally independently replaced with a —F, and wherein said cycloalkyl, cycloalkenyl, bi-or tricycloalkyl, bi- or tricycloalkenyl, heterocycloalkyl, aryl and heteroaryl of $R^9$ and $R^{10}$ are each optionally independently substituted with from one to three substituents independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —F, —Cl, —Br, —I, —OH, —CN, —NO$_2$, —NR$^{14}$R$^{15}$, —C(=O)NR$^{14}$R$^{15}$, —C(=O)R$^{11}$, —C(=O)OR$^{12}$, —S(O)$_n$R$^{11}$, —S(O)$_2$NR$^{14}$R$^{15}$, —$C_1$-$C_6$ hydroxyalkyl, —($C_6$-$C_{14}$) aryloxy, -(5-14 membered) heteroaryloxy, —($C_{zero}$-$C_4$)-(($C_6$-$C_{14}$) aryl), —($C_{zero}$-$C_4$)-(5-14 membered heteroaryl), and wherein said alkyl, alkenyl and alkynl substituents of $R^9$ and $R^{10}$ are each optionally independently further substituted with from one to six atoms independently selected from —F, —Cl, —Br and —I;

or NR$^9$R$^{10}$ may optionally form a -(4-7 membered) heterocycloalkyl or -(4-7 membered) heterocycloalkenyl, wherein said heterocycloalkyl and heterocycloalkenyl each optionally independently contain one or two further heteroatoms independently selected from N, O and S, and wherein said heterocycloalkyl and heterocycloalkenyl are each optionally independently substituted with from one to three substituents independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkynyl, —F, —Cl, —Br, —I, —OH, —CN, —NO$_2$, —NR$^{14}$R$^{15}$, —C(=O)NR$^{14}$R$^{15}$, —C(=O)R$^{11}$, —C(=O)OR$^{12}$, —S(O)$_n$R$^{11}$, —S(O)$_2$NR$^{14}$R$^{15}$, —($C_{zero}$-$C_4$)-($C_6$-$C_{14}$ aryl), —($C_{zero}$-$C_4$)-((5-14 membered) heteroaryl), —$C_6$-$C_{14}$ aryloxy and -(5-14 membered) heteroaryloxy, and wherein said —$C_1$-$C_6$ alkyl, —$C_2$-$C_6$ alkenyl and —$C_2$-$C_6$ alkynyl substituents of NR$^9$R$^{10}$ are each optionally independently further substituted with from one to six atoms independently selected from —F, —Cl, —Br and —I;

$R^{11}$ and $R^{12}$ are each independently selected from H, —$C_1$-$C_6$ alkyl, —($C_{zero}$-$C_4$ alkylene)-($C_3$-$C_8$ cycloalkyl), —($C_{zero}$-$C_4$ alkylene)-($C_4$-$C_8$ cycloalkenyl), —($C_{zero}$-$C_4$ alkylene)-(($C_5$-$C_{11}$)bi- or tricycloalkyl), —($C_{zero}$-$C_4$ alkylene)-(($C_7$-$C_{11}$)bi- or tricycloalkenyl), —($C_{zero}$-$C_4$ alkylene)-((3-8 membered) heterocycloalkyl), —($C_{zero}$-$C_4$ alkylene)-($C_6$-$C_{10}$ aryl) and —($C_{zero}$-$C_4$ alkylene)-((5-14 membered) heteroaryl), wherein $R^{11}$ and $R^{12}$ are each optionally independently substituted with from one to three substituents independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —NO$_2$, —CF$_3$, —NR$^{14}$R$^{15}$, —C(=O)N NR$^{14}$R$^{15}$, —SO$_2$NR$^{14}$R$^{15}$, —C(=O)H, —C(=O)OH and —C(=O)O($C_1$-$C_6$ alkyl), and wherein said alkyl, alkenyl and alkynyl substituents of $R^{11}$ and $R^{12}$ are each optionally independently further substituted with from one to six —F, or with from one to two substituents independently selected from —$C_1$-$C_4$ alkoxy, or with an —OH;

$R^{13}$ is selected from —H, —$C_1$-$C_6$ alkyl, —$C_2$-$C_6$ alkenyl, and —$C_2$-$C_6$ alkynyl, —($C_{zero}$-$C_4$ alkylene)-($C_3$-$C_{12}$ cycloalkyl), —($C_{zero}$-$C_4$ alkylene)-($C_4$-$C_{12}$ cycloalkenyl), —($C_{zero}$-$C_4$ alkylene)-(($C_5$-$C_{20}$)bi- or tricycloalkyl), —($C_{zero}$-$C_4$ alkylene)-(($C_7$-$C_{20}$)bi- or tricycloalkenyl), —($C_{zero}$-$C_4$ alkylene)-((3-12 membered) heterocycloalkyl), —($C_{zero}$-$C_4$ alkylene)-((7-20 membered) heterobi- or heterotricycloalkyl), —($C_{zero}$-$C_4$ alkylene)-($C_6$-$C_{14}$ aryl) and —($C_{zero}$-$C_4$ alkylene)-((5-14 membered) heteroaryl), wherein each hydrogen atom of said alkyl alkenyl and alkynyl of $R^1$ is optionally independently replaced with a —F, and wherein $R^{13}$ is optionally independently substituted with from one to three substitutents independently selected from —OH, —$C_1$-$C_{12}$ alkyl, —$C_2$-$C_{12}$ alkenyl, —$C_2$-$C_{12}$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —F, —Cl, —Br, —I, —CN, —NO$_2$, —CF$_3$, —NR$^{14}$R$^{15}$, —C(=O)N NR$^{14}$R$^{15}$, —SO$_2$NR$^{14}$R$^{15}$, —C(=O)H, —C(=O)OH and —C(=O)O($C_1$-$C_6$ alkyl), wherein said alkyl, alkenyl and alkynyl substituents of $R^{13}$ are each optionally independently further substituted with from one to six —F, or with from one to two substituents independently selected from —$C_1$-$C_4$ alkoxy, or with an —OH;

$R^{14}$ and $R^{15}$ are each independently selected from —H, —$C_1$-$C_{20}$ alkyl, —$C_2$-$C_{20}$ alkenyl, —$C_2$-$C_{20}$ alkynyl, —C(=O)R$^{11}$, —S(O)$_n$R$^{11}$, —C(=O)OR$^{12}$, —S(O)$_2$NR$^{11}$R$^{12}$, —($C_{zero}$-$C_4$ alkylene)-($C_3$-$C_{12}$ cycloalkyl), —($C_{zero}$-$C_4$ alkylene)-($C_4$-$C_{12}$ cycloalkenyl), —($C_{zero}$-$C_4$ alkylene)-(($C_5$-$C_{20}$)bi- or tricycloalkyl), —($C_{zero}$-$C_4$ alkylene)-(($C_7$-$C_{20}$)bi- or tricycloalkenyl), —($C_{zero}$-$C_4$ alkylene)-((3-8 membered) heterocycloalkyl), —($C_{zero}$-$C_4$ alkylene)-($C_6$-$C_{14}$ aryl) and —($C_{zero}$-$C_4$ alkylene)-((5-14 membered) heteroaryl), wherein each hydrogen atom of said alkyl, alkenyl and alkynyl of $R^{14}$ and $R^{15}$ is optionally independently replaced with a —F, and wherein said cycloalkyl, cycloalkenyl, bi- or tricycloalkyl, bi- or tricycloalkenyl, heterocycloalkyl, aryl and heteroaryl of $R^{14}$ and $R^{15}$ are each optionally independently substituted with from one to three substituents independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkynyl, —F, —Cl, —Br, —I, —OH, —CN, —$NO_2$, —$NH_2$, —C(=O)H, —S(O)$_n$H, —C(=O)OH, —C(=O)$NH_2$, —S(O)$_2NH_2$, —($C_{zero}$-$C_4$ alkylene)-($C_6$-$C_{14}$ aryl), —($C_{zero}$-$C_4$ alkylene)-((5-14 membered) heteroaryl), —$C_6$-$C_{14}$ aryloxy and -(5-14 membered) heteroaryloxy, wherein each hydrogen atom of said alkyl, alkenyl, alkynl, alkoxy, alkenoxy, alkynoxy, hydroxyalkyl, hydroxyalkenyl and hydroxyalkynyl substituent of $R^{14}$ and $R^{15}$ is optionally independently replaced with a —F, and wherein said alkyl, alkenyl and alkynyl substituents of $R^{14}$ and $R^{15}$ are each optionally independently further substituted with from one to six atoms independently selected from —Cl, —Br and —I;

or $NR^{14}R^{15}$ may optionally independently form a (4-7 membered) heterocycloalkyl or (4-7 membered) heterocycloalkenyl, wherein said heterocycloalkyl and heterocycloalkenyl optionally independently contains from one to two further heteroatoms independently selected from N, O, and S, and wherein said heterocycloalkyl and heterocycloalkenyl is optionally independently substituted with one to three substituents independently selected from —$C_1$-$C_6$ alkyl, —$C_2$-$C_6$ alkenyl, —$C_2$-$C_6$ alkynyl, —$C_1$-$C_6$ alkoxy, —$C_2$-$C_6$ alkenoxy, —$C_2$-$C_6$ alkynoxy, —$C_1$-$C_6$ hydroxyalkyl, —$C_2$-$C_6$ hydroxyalkenyl, —$C_2$-$C_6$ hydroxyalkynyl, —F, —Cl, —Br, —I, —OH, —CN, —$NO_2$, —$NH_2$, —C(=O)H, —S(O)$_n$H, —C(=O)OH, —C(=O)$NH_2$, —S(O)$_2NH_2$, —($C_{zero}$-$C_4$ alkylene)-($C_6$-$C_{14}$ aryl), —($C_{zero}$-$C_4$ alkylene)-((5-14 membered) heteroaryl), —$C_6$-$C_{14}$ aryloxy and -(5-14 membered) heteroaryloxy, and wherein each hydrogen atom of said alkyl, alkenyl, alkynyl, alkoxy, alkenoxy, alkynoxy, hydroxyalkyl, hydroxyalkenyl and hydroxyalkynyl substituent of $NR^{14}R^{15}$ is optionally independently replaced with a —F, and wherein said alkyl, alkenyl and alkynyl substituents of $NR^{14}R^{15}$ are each optionally independently further substituted with from one to six substituents independently selected from —Cl, —Br, and —I; and n is in each instance an integer independently selected from zero, 1, 2 and 3;

or the pharmaceutically acceptable salts of such compounds.

2. A compound according to claim 1, wherein $R^6$ is selected from —H, methyl, ethyl, —F, —Cl, —Br and —$CF_3$; or a pharmaceutically acceptable salt thereof.

3. A compound according to claim 1, wherein $R^1$ is selected from —$C_2$-$C_{12}$ alkyl, —$C_3$-$C_8$ cycloalkyl, —$C_5$-$C_8$ cycloalkenyl, —($C_5$-$C_{11}$)bi- or tricycloalkyl, —($C_7$-$C_{11}$)bi- or tricycloalkenyl, (3-8 membered) heterocycloalkyl, (7-11 membered) heterobicycloalkyl, —$C_6$-$C_{10}$ aryl and -(5-10 membered) heteroaryl; or a pharmaceutically acceptable salt thereof.

4. A compound according to claim 1, wherein $R^1$ is $C_1$-$C_4$ alkyl substituted with $R^{1a}$, wherein $R^{1a}$ is selected from —($C_6$-$C_{10}$)aryl and -(5-10 membered) heteroaryl; or a pharmaceutically acceptable salt thereof.

5. A compound according to claim 1, wherein $R^1$ is a straight-chain $C_2$-$C_{10}$ alkyl or branched $C_3$-$C_{10}$ alkyl; or a pharmaceutically acceptable salt thereof.

6. A compound according to claim 1, wherein $R^1$ is selected from —($C_7$-$C_{11}$)bi- or tricycloalkyl and (7-11 membered) heterobicycloalkyl; or a pharmaceutically acceptable salt thereof.

7. A compound according to claim 6, wherein $R^1$ is 1,2,3,4-tetrahydronaphthalenyl or indanyl optionally substituted with 1 to 3 fluorine or chlorine atoms.

8. A compound according to claim 1, wherein $R^7$ is selected from —H, —$C_1$-$C_{12}$ alkyl, —$C2$-$C_{12}$ alkenyl, —$C_1$-$C_{20}$ alkoxy, —$C2$-$C_{20}$ alkenoxy, —F, —Cl, —Br, —I, —CN, —$NO_2$, —$C_3$-$C_{12}$cycloalkyl, -(3-12 membered) heterocycloalkyl, —$C_6$-$C_{14}$ aryl, —(5-15 membered) heteroaryl, —CHO, —C(=O)($C_1$-$C_{15}$ alkyl), —C(=O)((5-12 membered)heterocycloalkyl), —C(=O)($C_6$-$C_{14}$ aryl), —C(=O)((5 - 15 membered) heteroaryl), —C(=O)($C_5$-$C_{12}$ cycloalkyl), —C(=O)O($C_1$-$C_8$ alkyl), —C(=O)N($C_1$-$C_{10}$ alkyl)($C_1$-$C_{10}$ alkyl), —C(=O)N($C_1$-$C_{10}$ alkyl)($C_6$-$C_{10}$ aryl), —C(=O)NH($C_6$-$C_{10}$ aryl), —C(=O)N($C_1$-$C_{10}$ alkyl)((5-10 membered) heteroaryl), —C(=O)NH((5-10 membered) heteroaryl), —C(=O)N($C_1$-$C_{10}$ alkyl)((5-$_{10}$ membered) heterocycloalkyl), —C(=O)NH((5-10 membered) heterocycloalkyl), —C(=O)N($C_1$-$C_{10}$ alkyl)($C_5$-$C_{10}$ cycloalkyl), —C(=O)NH($C_5$-$C_{10}$ cycloalkyl), —S(O)$_n$($C_1$-$C_{15}$ alkyl), —S(O)$_n$($C_5$-$C_{12}$ cycloalkyl), —S(O)$_n$($C_6$-$C_{15}$ aryl) and —S(O)$_n$((5-10 membered) heteroaryl), wherein each hydrogen atom of said alkyl, alkenyl, alkoxy and alkenoxy of $R^7$ is optionally independently replaced with a —F, and wherein said cycloalkyl and heterocycloalkyl of $R^7$ are each optionally independently substituted with from one to six —F, and wherein said alkyl, alkenyl, cycloalkyl, heterocycloalkyl, aryl and heteroaryl of $R^7$ are each optionally independently substituted with from one to three substituents independently selected from —$C_1$-$C_6$ alkoxy, —$C2$-$C_6$ alkenoxy, —$C2$-$C_6$ alkynoxy, —F, —Cl, —Br, —I, —OH, —$NR^9R^{10}$, —(CH$_2$)$_{1-10}NR^9R^{10}$, —C(=O)$R^{11}$, —S(O)$_n$$R^{11}$, —C(=O)O$R^{11}$, —C(=O)$NR^9R^{10}$, —S(O)$_n$$NR^9R^{10}$—$C_3$-$C_{12}$ cycloalkyl, -(4-12 membered) heterocycloalkyl, -(4-12 membered) heterocycloalkoxy, —$C_6$-$C_{15}$ aryl, -(5-15 membered) heteroaryl, —$C_6$-$C_{12}$ aryloxy and -(6-12 membered) heteroaryloxy; or a pharmaceutically acceptable salt thereof.

9. A compound according to claim 1, wherein $R^5$ is hydrogen; or a pharmaceutically acceptable salt thereof.

10. A compound according to claim 1, wherein $R^4$ and $R^5$ are hydrogen; or a pharmaceutically acceptable salt thereof.

11. A pharmaceutical composition, comprising a gamma-secretase inhibiting amount of a compound according to claim 1, or a pharmaceutically acceptable salt thereof.

* * * * *